United States Patent
Dahlgren et al.

(10) Patent No.: US 7,850,742 B2
(45) Date of Patent: Dec. 14, 2010

(54) KERATIN DYEING COMPOUNDS, KERATIN DYEING COMPOSITIONS CONTAINING SAID COMPOUNDS, AND USE THEREOF

(75) Inventors: Richard Marc Dahlgren, Cincinnati, OH (US); William David Laidig, Hamilton, OH (US); Mu-ill Lim, West Chester, OH (US); Bryan Patrick Murphy, Loveland, OH (US); Guiru Zhang, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/463,761

(22) Filed: May 11, 2009

(65) Prior Publication Data

US 2009/0282622 A1 Nov. 19, 2009

Related U.S. Application Data

(60) Provisional application No. 61/053,723, filed on May 16, 2008, provisional application No. 61/090,942, filed on Aug. 22, 2008.

(51) Int. Cl.
*A61Q 5/10* (2006.01)
*C07D 231/44* (2006.01)
(52) U.S. Cl. ................. 8/405; 8/406; 8/408; 8/435; 8/570; 8/573; 548/371.7
(58) Field of Classification Search .............. 8/405, 8/406, 408, 435, 570, 573; 548/371.7
See application file for complete search history.

(56) References Cited

U.S. PATENT DOCUMENTS

| | | | |
|---|---|---|---|
| 5,061,289 A | 10/1991 | Clausen | |
| 5,663,366 A | 9/1997 | Neunhoeffer | |
| 6,090,162 A | 7/2000 | Maibru | |
| 6,118,008 A | 9/2000 | Malle | |
| 6,660,046 B1 | 12/2003 | Terranova | |
| 2002/0050013 A1* | 5/2002 | Vidal et al. | ................. 8/405 |
| 2006/0246022 A1* | 11/2006 | Bureiko et al. | ................. 424/62 |
| 2007/0050922 A1 | 3/2007 | Glenn, Jr. | |

FOREIGN PATENT DOCUMENTS

EP    1 586 303 A1    10/2005

OTHER PUBLICATIONS

STIC Search Report dated Feb. 3, 2010.*

* cited by examiner

*Primary Examiner*—Eisa B Elhilo
(74) *Attorney, Agent, or Firm*—Laura R. Grunzinger; Melissa G. Krasovec

(57) ABSTRACT

Compositions for the oxidative dyeing of keratin fibers, comprising a medium suitable for dyeing and at least one 3-substituted pyrazole keratin dyeing compound and derivatives thereof. A method for oxidative dyeing of keratin fibers, comprising applying such compositions in the presence of an oxidizing agent, for a period sufficient to develop the desired coloration.

12 Claims, No Drawings

KERATIN DYEING COMPOUNDS, KERATIN DYEING COMPOSITIONS CONTAINING SAID COMPOUNDS, AND USE THEREOF

CROSS REFERENCE TO RELATED APPLICATIONS

This application claims the benefit of U.S. provisional application No. 61/053,723, filed May 16, 2008 and U.S. provisional application No. 61/090,942 filed Aug. 22, 2008.

FIELD OF INVENTION

This invention relates to 3-substituted pyrazole keratin dyeing compounds and derivatives thereof and compositions for the oxidative dyeing of keratin fibers (preferably hair) comprising such compounds, and use thereof.

BACKGROUND OF THE INVENTION

The permanent alteration of the color of keratinous fibres, in particular human hair, by the application of hair dyes is well known. In order to provide the consumer with a permanent and intense hair color, a very complex chemical process is utilized. Permanent hair dyeing formulations typically comprise oxidative hair dye precursors, i.e., developers and couplers, which diffuse into the hair through the cuticle and into the cortex, where the precursors then react with an oxidising agent, such as hydrogen peroxide, and each other to form larger-sized dye molecules. More specifically, an oxidizing agent, such as hydrogen peroxide, activates a developer dye and the activated developer then reacts with a coupler dye to form a larger-sized dye molecule that imparts color to the hair. These larger-sized, resultant dye molecules provide permanent, wash-resistant color, because these dyes are too large to readily diffuse out of the hair during subsequent washing. Different combinations of developers and couplers produce different shades of hair color.

In order to achieve desirable shades in the red area, 1-hydroxyethyl-4,5-diaminopyrazole is used, by itself or in a mixture with other developer substances, in combination with suitable coupler substances. When 1-hydroxyethyl-4,5-diaminopyrazole is used with a standard oxidant system, i.e., ammonium hydroxide and hydrogen peroxide at pH 10, natural and fashionable red shades are achieved. However, there exists a need for additional dyeing compounds that can provide desirable red shades, particularly when used with other oxidant systems, i.e., ammonium carbonate, hydrogen peroxide, and, optionally, a radical scavenger at pH 9.0.

SUMMARY OF THE INVENTION

This invention relates to 3-substituted pyrazole keratin dyeing compounds and derivatives thereof according to the formulas defined herein. This invention also relates to a composition for the oxidative dyeing of keratin fibers, comprising a medium suitable for dyeing and 3-substituted pyrazole keratin dyeing compounds and derivatives thereof. This invention further relates to a method for the oxidative dyeing of keratin fibers, the method comprising applying such compositions to the keratin fibers, in the presence of an oxidizing agent, for a period of time sufficient to develop the desired coloration. The keratin dyeing compounds may act as a developer.

It is to be understood that within the scope of this invention, numerous potentially and actually tautomeric compounds are involved. Thus, for example, 2-mercaptopyridine (I) exists under known conditions in the pyridine-2-thione tautomer form (II).

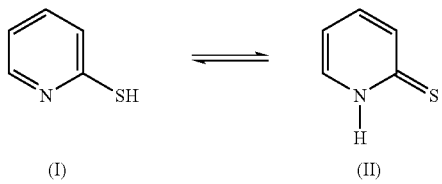

(I)          (II)

It is to be understood that when this development refers to a particular structure, all of the reasonable additional tautomeric structures are included. In the art, tautomeric structures are frequently represented by one single structure and the invention follows this general practice.

DETAILED DESCRIPTION OF THE INVENTION

While the specification concludes with claims that particularly point out and distinctly claim the invention, it is believed the invention will be better understood from the following description.

The invention relates to 3-substituted pyrazole keratin dyeing compounds and derivatives thereof. The compounds of the invention may act as developers that safely provide color benefits.

All percentages, parts and ratios are based upon the total weight of the compositions of the invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

Except as otherwise noted, all amounts including part, percentages, and proportions are understood to be modified by the word "about", and amounts are not intended to indicate significant digits. Except as otherwise noted, the articles "a", "an", and "the" mean "one or more".

As used herein, the term "keratin" refers to a scleroprotein found in epidermal tissues and modified into hard structures such as horns, hair, and nails. Thus, "keratinous fibers" refers to those found in hair, skin, and nails and various animal body parts such as horns, hooves and feathers.

As used herein, the term "hair" refers to keratinous fibers on a living, e.g. a person, or non-living body, e.g. in a wig, hairpiece, or other aggregation of non-living keratinous fibers. Mammalian, preferably human, hair is preferred. Notably, hair, wool, fur, and other keratinous fibers are suitable substrates for coloring by the compounds and compositions described herein.

As used herein, the term "keratin dyeing compounds" refers to compounds that may be used in the composition to act as developers, couplers, or both in order to provide color to ketatinous fibers.

As used herein, the term "keratin dyeing composition" refers to a composition containing one or more keratin dyeing compounds, including the compounds described herein.

As used herein, "cosmetically acceptable" means that ingredients which the term describes are suitable for use in contact with the skin or hair of humans and lower animals without undue toxicity, incompatibility, instability, irritation, allergic response, and the like.

I. Keratin Dyeing Compounds

The inventive compounds are 3-substituted pyrazole keratin dyeing compounds and derivatives thereof, according to the following formula:

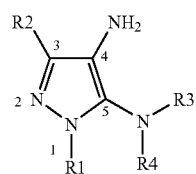

(I)

wherein R2 is selected from the group consisting of (i) substituted or unsubstituted alkynes, wherein substituents of the substituted alkynes are selected from the group consisting of alkyl (linear, branched, or cyclic C1-C10) aminoalkyl, hydroxyalkyl, dihydroxyalkyl, alkylaminoalkyl (linear, branched, or cyclic C1-C10), dialkylaminoalkyl (linear branched, or cyclic C1-C10), arylamino, hydroxyalkylaminoalkyl (linear, branched, or cyclic C1-C10), alkoxy, alkoxyalkyl (linear, branched, or cyclic C1-C10), dihydroxyalkylaminoalkyl (linear, branched, or cyclic C1-C5), aryl or substituted aryl (substituents are halogen, C1-C5 alkyl, C1-C5 alkoxy, trifluoromethyl, amino, C1-C5 alkylamino), heteroaryl or substituted heteroaryl (substituents are halogen, C1-C5 alkyl, C1-C5 alkoxy, trifluoromethyl, amino, C1-C5 alkylamino), arylmethyl or substituted arylmethyl (substituents are halogen, C1-C5 alkyl, C1-C5 alkoxy, trifluoromethyl, amino, C1-C5 alkylamino), heteroarylmethyl or substituted heteroarylmethyl (substituents are halogen, C1-C5 alkyl, C1-C5 alkoxy, trifluoromethyl, amino, C1-C5 alkylamino), and cyano;

(ii) substituted or unsubstituted alkenes, wherein substituents of the substituted alkynes are selected from the group consisting of alkyl (linear, branched, or cyclic C1-C10), aminoalkyl, hydroxyalkyl, dihydroxyalkyl, alkylaminoalkyl (linear, branched, or cyclic C1-C10), dialkylaminoalkyl (linear, branched, or cyclic C1-C10), arylamino, hydroxyalkylaminoalkyl (linear, branched, or cyclic C1-C10), alkoxy, alkoxyalkyl (linear, branched, or cyclic C1-C10), dihydroxyalkylaminoalkyl (linear, branched, or cyclic C1-C5), aryl or substituted aryl (substituents are halogen, C1-C5 alkyl, C1-C5 alkoxy, trifluoromethyl, amino, C1-C5 alkylamino), heteroaryl or substituted heteroaryl (substituents are halogen, C1-C5 alkyl, C1-C5 alkoxy, trifluoromethyl, amino, C1-C5 alkylamino), arylmethyl or substituted arylmethyl (substituents are halogen, C1-C5 alkyl, C1-C5 alkoxy, trifluoromethyl, amino, C1-C5 alkylamino), heteroarylmethyl or substituted heteroarylmethyl (substituents are halogen, C1-C5 alkyl, C1-C5 alkoxy, trifluoromethyl, amino, C1-C5 alkylamino), and cyano;

(iii) mono-, poly-, or per-halo alkyl systems, said halo group being fluoro or chloro, comprising from about 1 to about 10 carbon atoms;

(iv) S-linked monovalent substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;

(v) O-linked monovalent substituents selected from the group consisting of $OA^1$ and $ONA^1A^2$;

(vi) monovalent substituents selected from the group consisting of $COOA^1$, $CONA^1{}_2$ $CONA^1COA^2$, and CN;

(vii) a halogen selected from the group consisting of F, Cl, Br, and I;

wherein $A^1$ and $A^2$ are monovalent and are independently selected from the group consisting of H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, heterocyclic aryl or heterocyclic systems; and substituted or unsubstituted, mono-, poly-, or perfluoro alkyl systems; wherein said systems comprise from about 1 to about 10 carbon atoms and from about 0 to about 5 heteroatoms selected from the group consisting of O, S, N, P, and Si;

wherein R1, R3, and R4 are the same or different and are selected from the group consisting of:

(i) substituted or unsubstituted, straight or branched, alkyl, mono- or poly-unsaturated alkyl, heteroalkyl, aliphatic, heteroaliphatic, or heteroolefinic systems;

(ii) substituted or unsubstituted, mono- or poly-cyclic aliphatic, aryl, arylmethyl, heteroaryl, heteroarylmethyl, or heterocyclic systems;

(iii) mono-, poly-, or per-halo alkyl systems, said halo group being fluoro or chloro, comprising from about 1 to about 10 carbon atoms;

wherein said systems of (i) and (ii) comprise from about 1 to about 10 carbon atoms and from about 0 to about 5 heteroatoms selected from the group consisting of O, S, N, P, and Si;

wherein substituents of the substituted systems are selected from the group consisting of alkyl (linear, branched, or cyclic C1-C10), aminoalkyl, hydroxyalkyl, dihydroxyalkyl, alkylaminoalkyl (linear, branched, or cyclic C1-C10), dialkylaminoalkyl (linear, branched, or cyclic C1-C10), arylamino, hydroxyalkylaminoalkyl (linear, branched, or cyclic C1-C10), alkoxyalkyl (linear, branched, or cyclic C1-C10), dihydroxyalkylaminoalkyl (linear, branched, or cyclic C1-C5), aryl or substituted aryl (substituents are halogen C1-C5 alkyl, C1-C5 alkoxy, trifluoromethyl, amino, C1-C5 alkylamino), heteroaryl or substituted heteroaryl (substituents are halogen, C1-C5 alkyl, C1-C5 alkoxy, trifluoromethyl, amino, C1-C5 alkylamino), arylmethyl or substituted arylmethyl (substituents are halogen, C1-C5 alkyl. C1-C5 alkoxy, trifluoromethyl, amino, C1-C5 alkylamino), and heteroarylmethyl or substituted heteroarylmethyl (substituents are halogen, C1-C5 alkyl, C1-C5 alkoxy, trifluoromethyl, amino, C1-C5 alkylamino); or R1 and R3, together with the pyrazole core ring, form a 5-8 membered heterobicyclic ring system optionally having 1-2 hetero atoms selected from the group consisting of O, S, and N; or R3 and R4, together with the nitrogen atom to which they are attached, form a 5-8 membered heterocyclic ring optionally having 1-2 hetero atoms selected from the group consisting of O, S, and N.

In certain embodiments, R1, R3, and R4 are each individually selected from the group consisting of a hydrogen atom, a halogen atom, a cyano substituent, a C1-C10 alkyl substituent, a trifluoromethyl substituent, an aminoalkyl substituent, a hydroxyalkyl substituent, a carboxyl substituent or its esters, an alkoxy substituent, an alkoxyalkyl substituent, a carbamoyl substituent, an alkylcarbamoyl substituent, a hydroxyalkylcarbamoyl substituent, an amido substituent, an alkylamido substituent, an alkylcarbonyl substituent, an alkoxycarbonyl substituent, an aryloxy substituent, an acyloxy substituent, an alkylthio substituent, an arylthio substituent, a heteroarylthio substituent, a heteroaryloxy substituent, a 3-, 4-, 5-, 6-, or 7-membered heterocycle having at least one nitrogen, oxygen, or sulfur atom, an aryl substituent, an arylmethyl substituent, a heteroaryl substituent, a heteroarylmethyl substituent, a sulfonyl substituent, a sulfinyl substituent, a sulfamoyl substituent, a siloxy substituent, an acyloxy substituent, a sulfonamide substituent, a ureido substituent, a sulfamoylamino substituent, an alkoxycarbonylamino substituent, an aryloxycarbonylamino substituent, an aryloxycarbonyl substituent, and a benzenesulfonamide substituent.

In some embodiments, R2 is selected from the group consisting of a halogen atom, a cyano substituent, a carboxyl substituent or its esters, an alkoxy substituent, an alkoxyalkyl substituent, a carbamoyl substituent, an alkylcarbamoyl substituent, a hydroxyalkylcarbamoyl substituent, an amido substituent, an alkylamido substituent, an alkylcarbonyl substituent, an alkoxycarbonyl substituent, an aryloxy substituent, an acyloxy substituent, an alkylthio substituent, an arylthio substituent, a heteroarylthio substituent, a heteroaryloxy substituent, a 3-, 4-, 5-, 6-, or 7-membered heterocycle having at least one nitrogen, oxygen, or sulfur atom, an aryl substituent, an arylmethyl substituent, a heteroaryl substituent, a heteroarylmethyl substituent, a sulfonyl substituent, a sulfinyl substituent, a sulfamoyl substituent, a siloxy substituent, an acyloxy substituent, a sulfonamide substituent, a ureido substituent, a sulfamoyl amino substituent, an alkoxycarbonylamino substituent, an aryloxycarbonylamino substituent, an aryloxycarbonyl substituent, and a benzenesulfonamide substituent.

In some embodiments, the keratin dyeing compound of the invention is selected from the group consisting of 4,5-diamino-1-methyl-1H-pyrazole-3-carbonitrile; 3-methoxy-1-propyl-1H-pyrazole-4,5-diamine; 3-methoxy-1-(2-methoxyethyl)-1H-pyrazole-4,5-diamine; 1-(2-aminoethyl)-3-methoxy-1H-pyrazole-4,5-diamine; 3-bromo-1-(2-hydroxyethyl)-1H-pyrazole-4,5-diamine; 8-methoxy-1,2,4,5-tetrahydropyrazolo[5,1-d][1,3,5]oxadiazepin-9-amine; 1-benzyl-3-(ethylthio)-$N^5$,$N^5$-dimethyl-1H-pyrazole-4,5-diamine; 1-methyl-3-phenoxy-1H-pyrazole-4,5-diamine; 1-(2-hydroxyethyl)-3-methoxy-1H-pyrazol-4,5-diamine; 1-cyclohexyl-3-methoxy-1H-pyrazole-4,5-diamine; 6-methoxy-1-methyl-2,3-dihydro-1H-imidazo[1,2-b]pyrazol-7-amine; 2-methoxy-4,5,6,7-tetrahydropyrazolo[1,5-a]pyrimidin-3-amine; 3-methoxy-1-(2-(methylamino)ethyl)-1H-pyrazole-4,5-diamine; 3-methoxy-1-octyl-1H-pyrazole-4,5-diamine; 3-methoxy-1-pentyl-1H-pyrazole-4,5-diamine; 1-(3-amino-2-hydroxypropyl)-3-methoxy-1H-pyrazol-4,5-diamine; 6-methoxy-2,3-dihydro-1H-imidazo[1,2-b]pyrazol-7-amine; 6-ethoxy-2,3-dihydro-1H-imidazo[1,2-b]pyrazol-7-amine; 3-methoxy-1-(2-(pyrrolidin-1-yl)ethyl)-1H-pyrazole-4,5-diamine; 1-(3-aminopropyl)-3-methoxy-1H-pyrazole-4,5-diamine; 3-methoxy-$N^5$,$N^5$-dimethyl-1-propyl-1H-pyrazole-4,5-diamine; 1-hexyl-3-methoxy-1H-pyrazole-4,5-diamine; 1-butyl-3-methoxy-1H-pyrazole-4,5-diamine; 5-(4,5-diamino-3-methoxy-1H-pyrazol-1-yl)pentan-1-ol; 3-methoxy-1-propyl-5-(pyrrolidin-1-yl)-1H-pyrazol-4-amine; 1-hexyl-3-methoxy-$N^5$-methyl-1H-pyrazole-4,5-diamine; 1-isopropyl-3-methoxy-1H-pyrazole-4,5-diamine; 1-ethyl-3-methoxy-1H-pyrazole-4,5-diamine; 1-(2,3-dihydroxypropyl)-3-methoxy-1H-pyrazol-4,5-diamine; 1-hexyl-3-methoxy-$N^5$,$N^5$-dimethyl-1H-pyrazole-4,5-diamine; 3-methoxy-1-(4-methoxybenzyl)-1H-pyrazole-4,5-diamine; 3-methoxy-1-(pyridin-2-yl)-1H-pyrazole-4,5-diamine; 3-methoxy-1-phenyl-1H-pyrazole-4,5-diamine; 3-methoxy-1-(pyrimidin-2-yl)-1H-pyrazole-4,5-diamine; 1-(4-ethylphenyl)-3-methoxy-1H-pyrazole-4,5-diamine; 3-methoxy-1-p-tolyl-1H-pyrazole-4,5-diamine; 1-(2,4-dimethylphenyl)-3-methoxy-1H-pyrazole-4,5-diamine; 3-methoxy-1-(pyridin-4-yl)-1H-pyrazole-4,5-diamine; 1-benzyl-3-methoxy-1H-pyrazole-4,5-diamine; 1-(4-aminobenzyl)-3-methoxy-1H-pyrazole-4,5-diamine; 3-cyano-1-(2-hydroxyethyl)-1-pyrazole-4,5-diamine; 1-butyl-3-cyano-1H-pyrazole-4,5-diamine; 3-cyano-1-phenyl-1H-pyrazol-4,5-diamine; 3-cyano-1-(pyridin-2-yl)-1H-pyrazol-4,5-diamine; 3-cyano-1-(2,4-dimethylphenyl)-1H-pyrazol-4,5-diamino; 3-cyano-1-p-tolyl-1H-pyrazol-4,5-diamine; 3-cyano-1-(4-methoxyphenyl)-1H-pyrazol-4,5-diamine; 1-(4-aminophenyl)-3-cyano-1H-pyrazol-4,5-diamine; 3-cyano-1-(4-(dimethylamino)phenyl)-1H-pyrazol-4,5-diamine; 3-cyano-$N^5$,$N^5$-dimethyl-1-phenyl-1H-pyrazol-4,5-diamine; 3-cyano-1H-dimethyl-1-pentyl-1H-pyrazol-4,5-diamine; 3-cyano-1-pentyl-5-(pyrrolidin-1-yl)-1H-pyrazol-4-amine; 3-cyano-1-octyl-1H-pyrazol-4,5-diamine; 3-cyano-1-hexyl-1H-pyrazol-4,5-diamine; 1-butyl-3-cyano-1H-pyrazol-4,5-diamine; 7-amino-6-cyano-2,3-dihydro-1H-imidazo[1,2-b]pyrazole; 3-amino-2-cyano-4,5,6,7-tetrahydropyrazolo[1,5-a]pyrimidine; 3-cyano-1-(4-methoxybenzyl)-1H-pyrazol-4,5-diamine; 1-benzyl-3-cyano-1H-pyrazol-4,5-diamine; 3-cyano-1-cyclohexyl-1H-pyrazol-4,5-diamine; 3-cyano-1-isopropyl-1H-pyrazol-4,5-diamine; 1-(3-aminopropyl)-3-cyano-1H-pyrazol-4,5-diamine; 3-cyano-$N^5$, 1-(diisopropyl)-1H-pyrazol-4,5-diamine; $N^5$, 1-diisopropyl-3-methoxy-1H-pyrazole-4,5-diamine; 3-bromo-$N^5$,1-diisopropyl-1H-pyrazole-4,5-diamine; 1-cyclohexyl-3-fluoro-$N^5$-isopropyl-1H-pyrazole-4,5-diamine; 1-methyl-3-(trifluoromethoxy)-1H-pyrazole-4,5-diamine; 1-pentyl-3-phenoxy-1H-pyrazole-4,5-diamine; 1-(3-methoxypropyl)-3-phenoxy-1H-pyrazole-4,5-diamine; 3-fluoro-1-octyl-1H-pyrazole-4,5-diamine; 3-chloro-1-hexyl-1H-pyrazole-4,5-diamine; 3-bromo-1-pentyl-1H-pyrazole-4,5-diamine; 3-fluoro-1-(2-hydroxyethyl)-1H-pyrazol-4,5-diamine; 3-chloro-1-(2-hydroxyethyl)-1H-pyrazol-4,5-diamine; 3-chloro-1-propyl-5-(pyrrolidin-1-yl)-1H-pyrazol-4-amine; 3-chloro-1-(4-hydroxybutyl)-1H-pyrazol-4,5-diamine; 3-fluoro-1-(3-(methylamino)propyl)-1H-pyrazole-4,5-diamine; 1-(3-(dimethylamino)propyl)-3-fluoro-$N^5$,$N^5$-dimethyl-1H-pyrazole-4,5-diamine; 6-chloro-1-methyl-2,3-dihydro-1H-imidazo[1,2-b]pyrazol-7-amine; 2-chloro-5,6,7,8-tetrahydro-4H-pyrazolo[1,5-a][1,3]diazepin-3-amine; 2-methoxy-5,6,7,8-tetrahydro-4H-pyrazolo[1,5-a][1,3]diazepin-3-amine; 2-methoxy-4-methyl-5,6,7,8-tetrahydro-4H-pyrazolo[1,5-a][1,3]diazepin-3-amine; 3-chloro-1-(pyridin-2-yl)-1H-pyrazole-4,5-diamine; 1-(5-aminopyridin-2-yl)-3-fluoro-1H-pyrazole-4,5-diamine; 3-fluoro-1-(4-methoxybenzyl)-1H-pyrazole-4,5-diamine; 3-chloro-1-phenyl-1H-pyrazole-4,5-diamine; 3-bromo-1-p-tolyl-1H-pyrazole-4,5-diamine; 1-benzyl-3-bromo-1H-pyrazole-4,5-diamine; 1-pentyl-3-phenoxy-1H-pyrazole-4,5-diamine; 1-(3-methoxypropyl)-3-phenoxy-1H-pyrazole-4,5-diamine; 1-(3-hydroxypropyl)-3-phenoxy-1H-pyrazole-4,5-diamine; 1-(3-aminopropyl)-$N^5$-methyl-3-phenoxy-1H-pyrazole-4,5-diamine; 3-chloro-$N^5$,$N^5$-dimethyl-1-pentyl-1H-pyrazole-4,5-diamine; 1-(3,5-dimethoxyphenyl)-3-fluoro-1H-pyrazole-4,5-diamine; 3-fluoro-1-methyl-1H-pyrazole-4,5-diamine; 3-chloro-1-ethyl-1H-pyrazole-4,5-diamine; 1-hexyl-3-(methylsulfonyl)-1H-pyrazole-4,5-diamine; 3-(methylsulfinyl)-1-octyl-1H-pyrazole-4,5- diamine; 1-cyclohexyl-3-(methylsulfonyl)-1H-pyrazole-4,5-diamine; 3-(methylsulfonyl)-1-phenyl-1H-pyrazole-4,5-diamine; 3-(methylsulfonyl)-1-propyl-1H-pyrazole-4,5-diamine; 1-(3-methoxypropyl)-3-(methylsulfinyl)-1H-pyrazole-4,5-diamine; 1-(3-hydroxypropyl)-3-(methylsulfinyl)-1H-pyrazole-4,5-diamine; 3-(methylsulfonyl)-1-propyl-5-(pyrrolidin-1-yl)-1H-pyrazol-4-amine; 1-butyl-3-(methylsulfonyl)-5-(piperidin-1-yl)-1H-pyrazol-4-amine; 1-methyl-3-(methylsulfonyl)-5-morpholino-1H-pyrazol-4-amine; 5-(4-ethylpiperazin-1-yl)-1-methyl-3-(methyl sulfonyl)-1H-pyrazol-4-amine; 1-(4-(dimethylamino)phenyl)-3-(methylsulfonyl)-1H-pyrazole-4,5-diamine; 1-(4-methoxybenzyl)-3-(methylsulfonyl)-1H-pyrazole-4,5-diamine; $N^5$,1-diisopropyl-3-(methylsulfonyl)-1H-pyrazole-4,5-diamine; $N^5$,$N^5$-dimethyl-3-(methylsulfonyl)-1-pentyl-1H-pyrazole-4,5-diamine; 3-(methylsulfonyl)-1-o-tolyl-1H-pyrazole-4,5-diamine; 3-(methylsulfonyl)-1-(pyridin-2-yl)-1H-pyrazole-4,5-diamine; 3-(methylsulfinyl)-1-(pyrimidin-2-yl)-1H-pyrazole-4,5-diamine; 3-(methylsulfinyl)-1-(thiazol-2-yl)-1H-pyrazole-4,5-diamine; 1-(1-methyl-1H-imidazol-2-yl)-3-(methylsulfinyl)-1H-pyrazole-4,5-diamine; 3-(methylsulfonyl)-1-(thiazol-2-yl)-1H-pyrazole-4,5-diamine; 2-(methylsulfonyl)-5,6,7,8-tetrahydro-4H-pyrazolo[1,5-a][1,3]diazepin-3-amine; 6-(methylsulfonyl)-2,3-dihydro-1H-imidazo[1,2-b]pyrazol-7-amine; 1-methyl-3-(methylsulfinyl)-1H-pyrazole-4,5-diamine; 1-methyl-3-(methylsulfonyl)-1H-pyrazole-4,5-diamine; 1-(3-(methylamino)propyl)-3-(methylsulfonyl)-1H-pyrazole-4,5-diamine; 1-(2-aminoethyl)-3-(methylsulfinyl)-1H-pyrazole-4,5-diamine; 1-hexyl-3-(trifluoromethoxy)-1H-pyrazole-4,5-diamine; 2-(4,5-diamino-3-ethynyl-pyrazol-1-yl)-ethanol; 5-ethynyl-2-methyl-2H-pyrazole-3,4-diamine; 5-ethynyl-2-(2-methoxy-ethyl)-2H-pyrazole-3,4-diamine; 5-ethynyl-2-hexyl-2H-pyrazole-3,4-diamine; 5-ethynyl-2-phenyl-2H-pyrazole-3,4-diamine; 2-(4,5-diamino-3-phenylethynyl-pyrazol-1-yl)-ethanol; 2-benzyl-5-prop-1-ynyl-2H-pyrazole-3,4-diamine; 5-ethynyl-2-pyridin-2-yl-2H-pyrazole-3,4-diamine; 5-ethynyl-2-(1H-imidazol-4-ylmethyl)-2H-pyrazole-3,4-diamine; and 5-(4,5-diamino-3-ethynyl-pyrazol-1-yl)-pentane-1,2-diol.

In certain preferred embodiments, the keratin dyeing compound of the invention is selected from the group consisting of 4,5-diamino-1-methyl-1H-pyrazole-3-carbonitrile; 3-methoxy-1-propyl-1H-pyrazole-4,5-diamine; 3-methoxy-1-(2-methoxyethyl)-1H-pyrazole-4,5-diamine; 1-(2-aminoethyl)-3-methoxy-1H-pyrazole-4,5-diamine; 8-methoxy-1,2,4,5-tetrahydropyrazolo[5,1-d][1,3,5]oxadiazepin-9-amine; 1-(2-hydroxyethyl)-3-methoxy-1H-pyrazol-4,5-diamine; 1-cyclohexyl-3-methoxy-1H-pyrazole-4,5-diamine; 6-methoxy-1-methyl-2,3-dihydro-1H-imidazo[1,2-b]pyrazol-7-amine; 2-methoxy-4,5,6,7-tetrahydropyrazolo[1,5-a]pyrimidin-3-amine; 3-methoxy-1-octyl-1H-pyrazole-4,5-diamine; 3-methoxy-1-pentyl-1H-pyrazole-4,5-diamine; 6-methoxy-2,3-dihydro-1H-imidazo[1,2-b]pyrazol-7-amine; 3-methoxy-$N^5$,$N^5$-dimethyl-1-propyl-1H-pyrazole-4,5-diamine; 1-hexyl-3-methoxy-1H-pyrazole-4,5-diamine; 1-butyl-3-methoxy-1H-pyrazole-4,5-diamine; 1-isopropyl-3-methoxy-1H-pyrazole-4,5-diamine; 1-ethyl-3-methoxy-1H-pyrazole-4,5-diamine; 3-methoxy-1-(4-methoxybenzyl)-1H-pyrazole-4,5-diamine; 3-methoxy-1-(pyridin-2-yl)-1H-pyrazole-4,5-diamine; 1-(4-ethylphenyl)-3-methoxy-1H-pyrazole-4,5-diamine; 3-methoxy-1-p-tolyl-1H-pyrazole-4,5-diamine; 3-cyano-1-(2-hydroxyethyl)-1H-pyrazole-4,5-diamine; 1-butyl-3-cyano-1H-pyrazole-4,5-diamine; 3-cyano-1-phenyl-1H-pyrazole-4,5-diamine; 3-cyano-1-hexyl-1H-pyrazole-4,5-diamine; 1-butyl-3-cyano-1H-pyrazol-4,5-diamine; 3-cyano-1-(4-methoxybenzyl)-1H-pyrazol-4,5-diamine; 3-cyano-1-isopropyl-1H-pyrazol-4,5-diamine; 1-cyclohexyl-3-fluoro-$N^5$-isopropyl-1H-pyrazole-4,5-diamine; 1-methyl-3-(trifluoromethoxy)-1H-pyrazole-4,5-diamine; 3-fluoro-1-octyl-1H-pyrazole-4,5-diamine; 3-chloro-1-hexyl-1H-pyrazole-4,5-diamine; 3-fluoro-1-(2-hydroxyethyl)-1H-pyrazol-4,5-diamine; 3-chloro-1-(2-hydroxyethyl)-1H-pyrazol-4,5-diamine; 3-chloro-1-(4-hydroxybutyl)-1H-pyrazol-4,5-diamine; 3-chloro-1-(pyridin-2-yl)-1H-pyrazole-4,5-diamine; 3-chloro-1-phenyl-1-pyrazole-4,5-diamine; 3-chloro-1-ethyl-1H-pyrazole-4,5-diamine; 1-(3-methoxypropyl)-3-(methylsulfinyl)-1H-pyrazole-4,5-diamine; 1-(3-hydroxypropyl)-3-(methylsulfinyl)-1H-pyrazole-4,5-diamine; 1-(4-methoxybenzyl)-3-(methylsulfonyl)-1H-pyrazole-4,5-diamine; and 1-methyl-3-(methylsulfonyl)-1H-pyrazole-4,5-diamine.

SYNTHESIS EXAMPLES

The following are non-limiting synthesis examples of the keratin dyeing compounds.

Example A 4,5-Diamino-1-methyl-1H-pyrazole-3-carbonitrile, obtainable from the following synthesis strategy

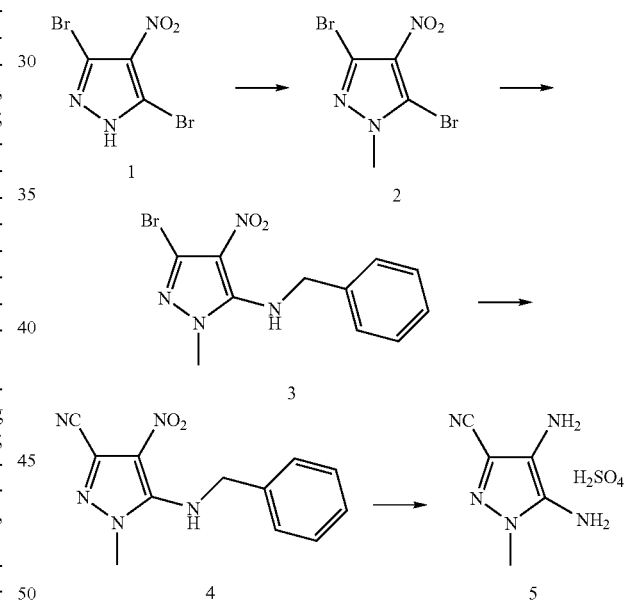

Preparation of 3,5-dibromo-1-methyl-4-nitro-1H-pyrazole (2): To a solution of 3,5-dibromo-4-nitropyrazole 1 (0.934 g, 3.45 mmol) in 5 mL of absolute DMF were added dropwise 0.16 g of sodium hydride (6.67 mmol) in DMF (100 mL) over a period of 1 h. After cessation of gas generation, 0.26 mL of $CH_3I$ (3.89 mmole) was added dropwise and stirred at room temperature for overnight. The solvent was then evaporated under vacuum and the residue was poured into water, The separated solid was filtered, washed with water and dried under vacuum to afford 0.713 g of 2 (yield 72.6%).

Preparation of N-benzyl-3-bromo-1-methyl-4-nitro-1H-pyrazol-5-amine (3): 3,5-dibromo-1-methyl-4-nitropyzole 2 (2.85 g 10 mmol) was heated in a solution of 10 mL of benzylamine for 6 h at 80° C. After cooling to room temperature, the reaction mixture was poured into water and the yellow solid formed. Then it was filtered, washed with water, dried and recrystallized from toluene to afford 3 g of 3 in yield of 96%.

Preparation of 5-amino-1-methyl-4-nitro-1H-pyrazole-3-carbonitrile (4): A mixture of CuCN (0.135 g, 1.5 mmol) and 3 (0.312 g, 1 mmol) in solution of DMF (10 mL) were refluxed for 8 h before it was poured on water and filtered. The filtrate and the separated yellow solid, which was dissolved in concentrated ammonium hydroxide, were extracted by EtOAc. The organic layer was dried using $Na_2SO_4$ and purified by flash column chromatography (EtOAc: PE=2:1~1:1) to afford 0.108 g of 4 in yield of 42%.

Preparation of 4,5-diamino-3-cyano-1-methylpyrazole (5): A mixture 4 (0.257 g, 1 mmol) and 10% Pd/C (0.3 g) catalyst in 20 mL ethanol were stirred in hydrogen atmosphere at room temperature for 48 h. After filtration, the solvent was removed under reduced pressure to 2-3 mL before 98% $H_2SO_4$ was added dropwise until pH=1. The formed solid was filtered and washed with small amount of ethanol to afford 0.106 g of 5 in yield of 45%: $^1$HNMR (300 MHz, DMSO-$d_6$) δ 3.00 (3H); $^{13}$CNMR (75 MHz, DMSO-$d_6$) δ 35.9, 110.3, 114.2, 114.5, 138.4; MS (EI) 137.

Example B

3-Methoxy-1-propyl-1H-pyrazole-4,5-diamine, obtainable from the following synthetic strategy

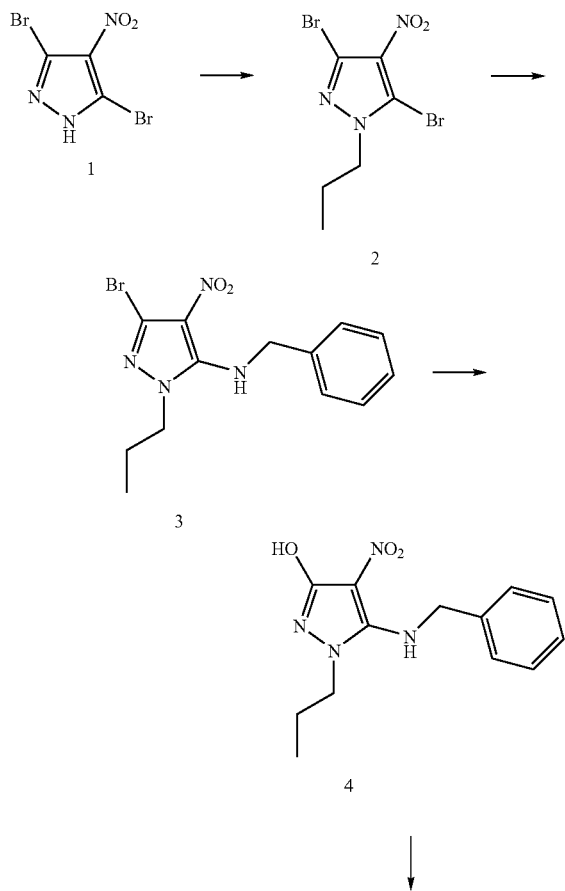

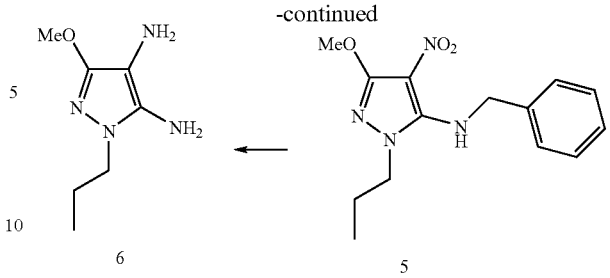

Treatment of 3,5-dibromo-4-nitro-1H-pyrazole 1 with 1-propyl bromide and NaH in DMF affords 3,5-dibromo-1-propyl-4-nitro-1H-pyrazole 2. Nucleophilic aromatic substitution of the compound 2 with benzylamine in DMSO produces benzyl-(5-bromo-2-propyl-4-nitro-2H-pyrazol-3-yl)-amine 3. The reaction of the compound 3 with KOH in the presence of $Pd_2 dba_3$ and 2-di-tert-butylphosphino-2',4',6'-tri isopropyl-biphenyl in 1,4-dioxane/water provides 5-(benzylamino)-4-nitro-1-propyl-1H-pyrazol-3-ol 4, which upon treatment with MeI and cetylammonium bromide in 1,4-dioxane/water/KOH affords compound 5 (J. Am. Chem. Soc. 2006, 128, 10694). Hydrogenation of the compound 5 with 10% Pd/C at 60 psi of hydrogen in MeOH gives 3-methoxy-1-propyl-1H-pyrazole-4,5-diamine 6.

Example C 2-(4,5-Diamino-3-bromo-1H-pyrazol-1-yl)ethanol, obtainable from the following synthetic strategy

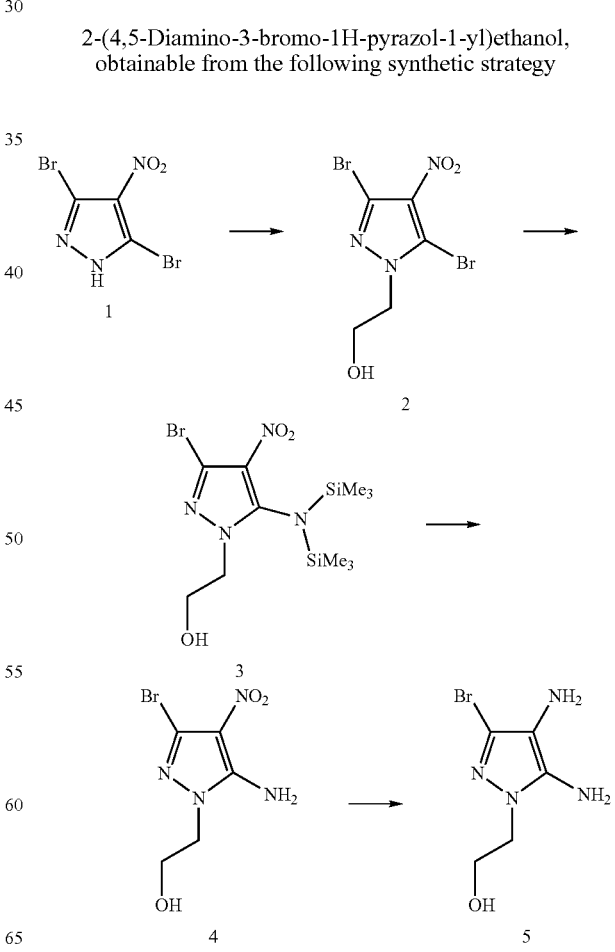

Treatment of 3,5-dibromo-4-nitro-1H-pyrazole 1 with 2-bromoethanol and NaH in DMF affords 2-(3,5-dibromo-4-nitro-1H-pyrazol-1-yl)ethanol 2. Reaction of the compound 2 with lithium bis(trimethylsilyl)amide in the presence of bis(dibenzylidene)palladium (0) and P(t-Bu)$_3$ in toluene affords the bis-silylamine 3, which is readily converted to 2-(5-amino-3-bromo-4-nitro-1H-pyrazol-1-yl)ethanol 4 by addition of aqueous HCl and neutralization (Org. Lett. 2001, 3, 2729). Reduction of the compound 4 with Fe in acetic acid provides 2-(4,5-diamino-3-bromo-1H-pyrazol-1-yl)ethanol 5.

Example D

8-Methoxy-1,2,4,5-tetrahydropyrazolo[5,1-d][1,3,5]oxadiazepin-9-amine, obtainable from the following synthetic strategy

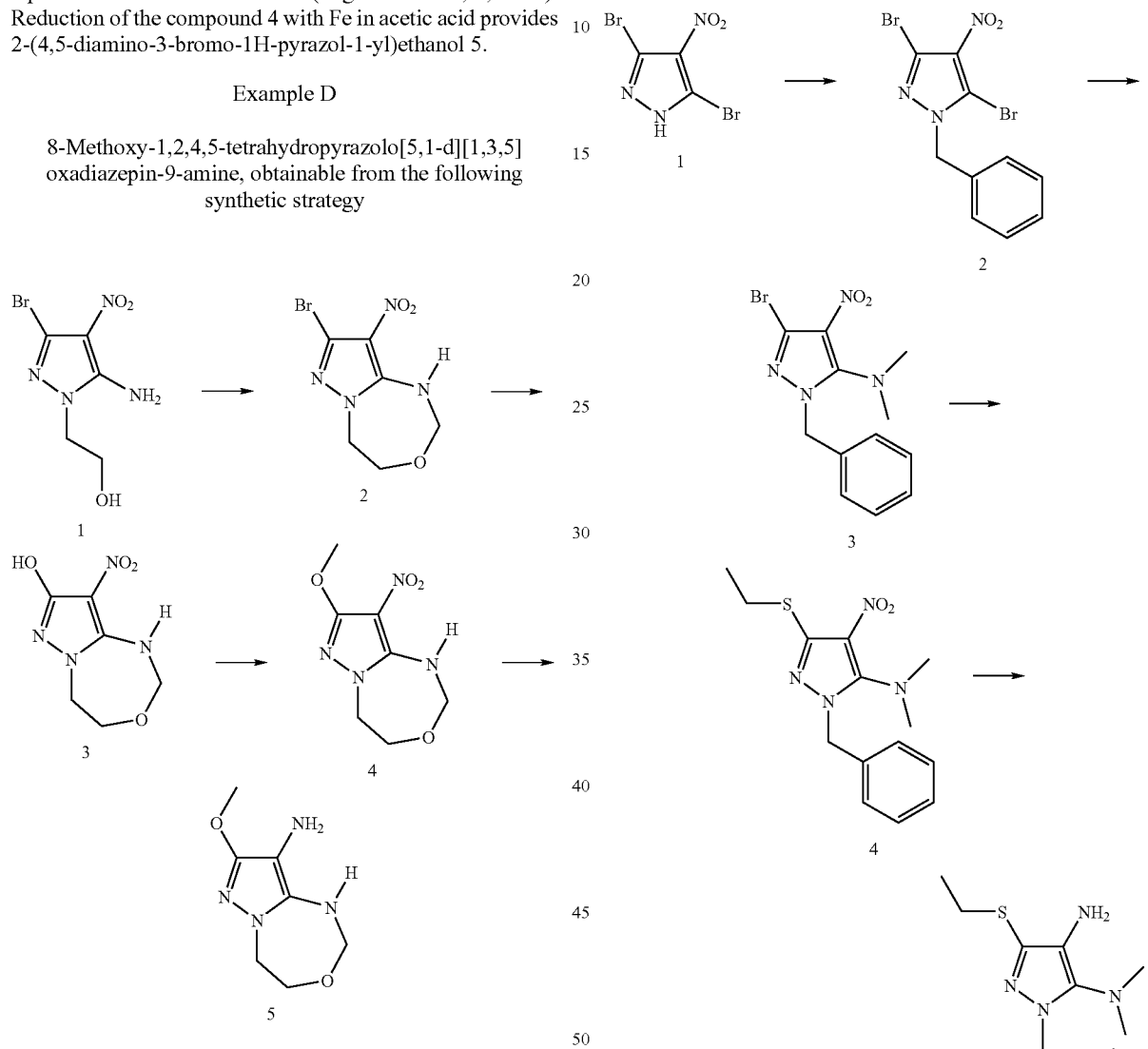

Treatment of 2-(5-amino-3-bromo-4-nitro-1H-pyrazol-1-yl)ethanol 1 with paraformaldehyde and sodium triacetoxyborohydride in dichloroethane containing acetic acid affords 8-bromo-9-nitro-1,2,4,5-tetrahydropyrazolo[5,1-d][1,3,5]oxadiazepine 2. The reaction of the compound 2 with KOH in the presence of Pd$_2$dba$_3$ and 2-di-tert-butylphosphino-2',4',6'-triisopropylbiphenyl in 1,4-dioxane, water provides 9-nitro-1,2,4,5-tetrahydropyrazolo[5,1-d][1,3,5]oxadiazepin-8-ol 3, which upon treatment with MeI and cetylammonium bromide in 1,4-dioxane/water/KOH affords compound 8-methoxy-9-nitro-1,2,4,5-tetrahydropyrazolo[5,1-d][1,3,5]oxadiazepine 4 (J. Am. Chem. Soc. 2006, 128, 10694). Hydrogenation of 4 with Pd/C at 60 psi of hydrogen yields 8-methoxy-1,2,4,5-tetrahydropyrazolo[5,1-d][1,3,5]oxadiazepin-9-amine 5.

Example E

1-Benzyl-3-(ethylthio)-N$^5$,N$^5$-dimethyl-1H-pyrazole-4,5-diamine, obtainable from the following synthetic strategy

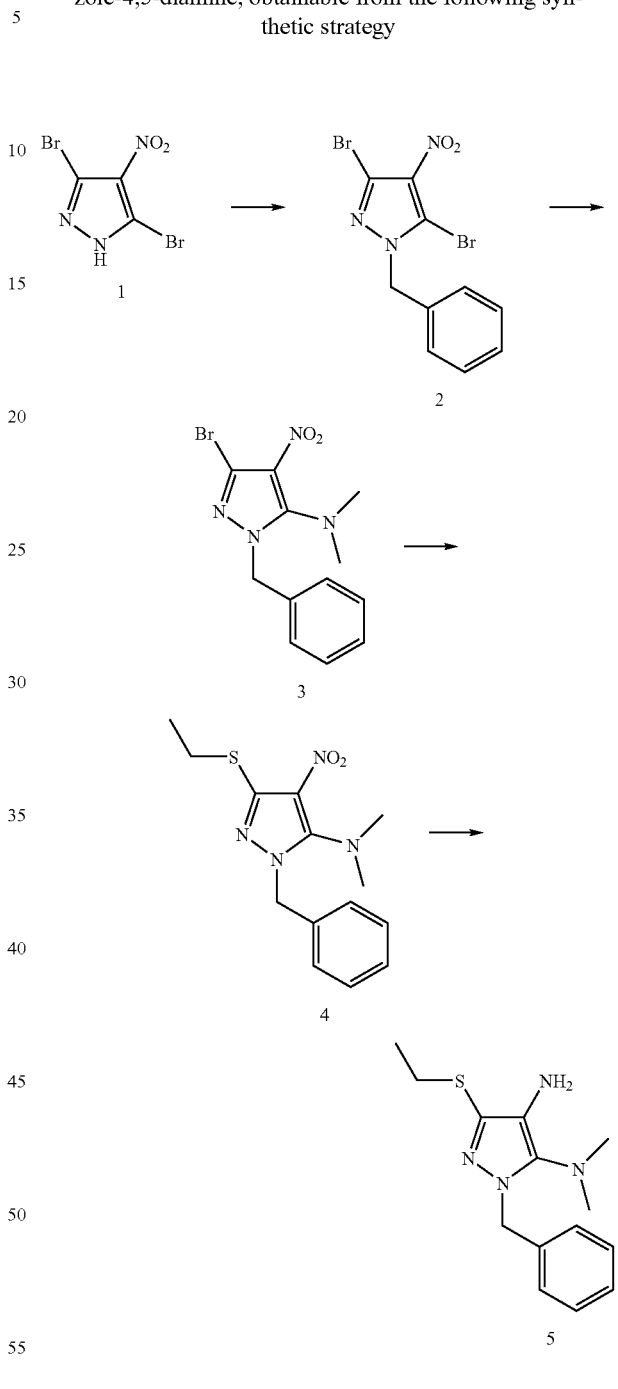

Treatment of 3,5-dibromo-4-nitro-1H-pyrazole 1 with benzyl bromide and NaH in DMF affords 1-benzyl-3,5-dibromo-4-nitro-1H-pyrazole 2. Nucleophilic aromatic substitution of the compound 2 with dimethylamine in DMSO gives 1-benzyl-3-bromo-N,N-dimethyl-4-nitro-1H-pyrazol-5-amine 3. The compound 3 is treated with ethanethiol in the presence of CoI$_2$(PPh$_3$)$_2$, zinc and pyridine in acetonitrile (Org. Lett. 2006, 8, 5613) to afford 1-benzyl-3-(ethylthio)-N,N-dimethyl-4-nitro-1H-pyrazol-5-amine 4. Hydrogenation of the compound 4 with Pd/C at 60 psi hydrogen in ethanol affords 1-benzyl-3-(ethylthio)-$N^5,N^5$-dimethyl-1H-pyrazole-4,5-diamine 5.

Example F

1-Methyl-3-phenoxy-1H-pyrazole-4,5-diamine, obtainable from the following synthetic strategy

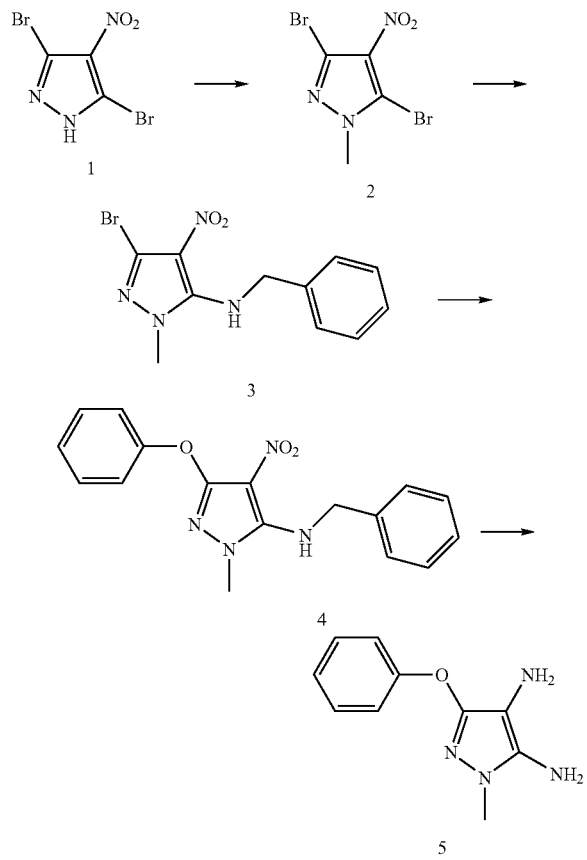

Treatment of 3,5-dibromo-4-nitro-1H-pyrazole 1 with MeI and NaH in DMF affords 3,5-dibromo-1-methyl-4-nitro-1H-pyrazole 2. Nucleophilic aromatic substitution of the compound 2 with benzylamine in DMSO produces benzyl-(5-bromo-2-methyl-4-nitro-2H-pyrazol-3-yl)-amine 3. Treatment of the compound 3 with phenol in the presence of copper (I) iodide and cecium carbonate in N-methylpyrrolidinone (NMP) under microwave irradiation provides N-benzyl-1-methyl-4-nitro-3-phenoxy-1H-pyrazol-5-amine 4 (Tetrahedron Lett, 2003, 44, 3445). Hydrogenation of the compound 4 with Pd/C at 60 psi hydrogen in ethanol affords 1-methyl-3-phenoxy-1H-pyrazole-4,5-diamine 5.

II. Keratin Dyeing Composition Components

The inventive compositions for the oxidative dyeing of keratin fibers comprise the hair-dyeing compound described above and a medium suitable for dyeing. The inventive compositions may further comprise additional components known, conventionally used, or otherwise effective for use in oxidative dye compositions, including but not limited to: developer dye compounds; coupler dye compounds; direct dyes; oxidizing agents; thickeners; chelants; pH1 modifiers and buffering agents; carbonate ion sources; radical scavengers; anionic, cationic, nonionic, amphoteric or zwitterionic surfactants, or mixtures thereof, anionic, cationic, nonionic, amphoteric or zwitterionic polymers, or mixtures thereof, fragrances; buffers; dispersing agents; peroxide stabilizing agents; natural ingredients, e.g. proteins and protein derivatives, and plant materials (e.g. aloe, chamomile and henna extracts); silicones (volatile or non-volatile, modified or non-modified), film-forming agents, ceramides, preserving agents; and opacifiers.

Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

A. Medium Suitable for Dyeing

The medium suitable for dyeing may be selected from water, or a mixture of water and at least one organic solvent to dissolve the compounds that would not typically be sufficiently soluble in water. Suitable organic solvents for use herein include, but are not limited to: C1 to C4 lower alkanols (e.g., ethanol, propanol, isopropanol), aromatic alcohols (e.g. benzyl alcohol and phenoxyethanol); polyols and polyol ethers (e.g., carbitols, 2-butoxyethanol, propylene glycol, propylene glycol monomethyl ether, diethylene glycol monoethyl ether, monomethyl ether, hexylene glycol, glycerol, ethoxy glycol), and propylene carbonate. When present, organic solvents are typically present in an amount ranging from 1% to 30%, by weight of the composition. Preferred solvents are water, ethanol, propanol, isopropanol, glycerol, 1,2-propylene glycol, hexylene glycol, ethoxy diglycol, and mixtures thereof.

B. Developers

Suitable developers for use in the compositions described herein include, but are not limited to, p-phenylenediamine derivatives, e.g. benzene-1,4-diamine (commonly known as p-phenylenediamine); 2-chloro-benzene-1,4-diamine; N-phenyl-benzene-1,4-diamine; N-(2-ethoxyethyl)benzene-1,4-diamine; 2-[(4-amino-phenyl)-(2-hydroxy-ethyl)-amino]-ethanol (commonly known as N,N-bis(2-hydroxyethyl)-p-phenylenediamine); (2,5-diamino-phenyl)-methanol; 1-(2'-Hydroxyethyl)-2,5-diaminobenzene; 2-(2,5-diamino-phenyl)-ethanol; N-(4-aminophenyl)benzene-1,4-diamine; 2,6-dimethyl-benzene-1,4-diamine; 2-isopropyl-benzene-1,4-diamine; 1-[(4-aminophenyl)amino]-propan-2-ol; 2-propyl-benzene-1,4-diamine; 1,3-bis[(4-aminophenyl)(2-hydroxyethyl)amino]propan-2-ol; $N^4,N^4,2$-trimethylbenzene-1,4-diamine; 2-methoxy-benzene-1,4-diamine; 1-(2,5-diaminophenyl)ethane-1,2-diol; 2,3-dimethyl-benzene-1,4-diamine; N-(4-amino-3-hydroxyphenyl)-acetamide; 2,6-diethylbenzene-1,4-diamine; 2,5-dimethylbenzene-1,4-diamine; 2-thien-2-ylbenzene-1,4-diamine; 2-thien-3-ylbenzene-1,4-diamine; 2-pyridin-3-ylbenzene-1,4-diamine; 1,1-biphenyl-2,5-diamine; 2-(methoxymethyl)benzene-1,4-diamine; 2-(aminomethyl)benzene-1,4-diamine; 2-(2,5-diaminophenoxy)ethanol; N-[2-(2,5-diaminophenoxy)ethyl]-acetamide; N,N-dimethylbenzene-1,4-diamine; N,N-diethylbenzene-1,4-diamine; N,N-dipropylbenzene-1,4-diamine; 2-[(4-aminophenyl)(ethyl)amino]ethanol; 2-[(4-amino-3-methyl-phenyl)-(2-hydroxy-ethyl)-amino]-ethanol; N-(2-methoxyethyl)-benzene-1,4-diamine; 3-[(4-aminophenyl)amino]propan-1-ol; 3-[(4-aminophenyl)-amino]propane-1,2-diol; N-{4-[(4-aminophenyl)amino]butyl}benzene-1,4-diamine; 2-[2-(2-{2-[(2,5-diaminophenyl)-oxy]ethoxy}ethoxy)ethoxy]

benzene-1,4-diamine; 1,3-bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; p-aminophenol derivatives such as: 4-amino-phenol (commonly known as p-aminophenol); 4-methylamino-phenol; 4-amino-3-methyl-phenol; 4-amino-2-hydroxymethyl-phenol; 4-amino-2-methyl-phenol; 4-amino-1-hydroxy-2-(2'-hydroxyethylaminomethyl)benzene; 4-amino-2-methoxymethyl-phenol; 5-amino-2-hydroxy-benzoic acid; 1-(5-amino-2-hydroxy-phenyl)-ethane-1,2-diol; 4-amino-2-(2-hydroxy-ethyl)-phenol; 4-amino-3-(hydroxymethyl)phenol; 4-amino-3-fluoro-phenol; 4-amino-2-(aminomethyl)-phenol; 4-amino-2-fluoro-phenol; 1-hydroxy-2,4-diaminobenzene; o-phenylenediamine derivatives such as: 3,4-Diaminobenzoic acid and salts thereof, o-aminophenol derivatives such as: 2-amino-phenol (commonly known as o-aminophenol); 2,4-diaminophenol; 2-amino-5-methyl-phenol; 2-amino-5-ethyl-phenol; 2-amino-6-methyl-phenol; N-(4-amino-3-hydroxy-phenyl)-acetamide; and 2-amino-4-methyl-phenol; and heterocyclic derivatives such as: pyrimidine-2,4,5,6-tetramine (commonly known as 2,4,5,6-tetraminopyrimidine); 1-methyl-1H-pyrazole-4,5-diamine; 2-(4,5-diamino-1H-pyrazol-1-yl)ethanol; $N^2$, $N^2$-dimethyl-pyridine-2,5-diamine; 2-[(3-amino-6-methoxypyridin-2-yl)amino]ethanol; 6-methoxy-$N^2$-methyl-pyridine-2,3-diamine; 2,5,6-triaminopyrimidin-4(1H)-one; pyridine-2,5-diamine; 1-isopropyl-1H-pyrazole-4,5-diamine; 1-(4-methylbenzyl)-1H-pyrazole-4,5-diamine; 1-(benzyl)-1H-pyrazole-4,5-diamine; 1-(4-chlorobenzyl)-1H-pyrazole-4,5-diamine; pyrazolo[1,5-a]-pyrimidine-3,7-diamine; 5,6,7-trimethylpyrazolo[1,5-a]pyrimidin-3-ylamine hydrochloride; 7-methylpyrazolo[1,5-a]pyrimidin-3-ylamine hydrochloride; 2,5,6,7-teramethylpyrazolo[1,5-a]pyrimidin-3-ylamine hydrochloride; 5,7-di-tert-butylpyrazolo[1,5-a]pyrimidin-3-ylamine hydrochloride; 5,7-di-trifluoromethyl-pyrazolo[1,5-a]pyrimidin-3-ylamine hydrochloride; 2-methylpyrazolo[1,5-a]pyrimidin-3,7-diamine hydrochloride; 4-hydroxy-2,5,6-triaminopyrimidine; 1-hydroxyethyl-4,5-diaminopyrazole sulphate; and 2,5-diaminophenylethyl alcohol.

Additional developers are selected from the group consisting of N-(3-furylmethyl)benzene-1,4-diamine; N-thiophen-3-ylmethyl-benzene-1,4-diamine; N-(2-furylmethyl)benzene-1,4-diamine; N-thiophen-2-ylmethyl-benzene-1,4-diamine; 3-(2,5-diamino-phenyl)-N-ethyl-acrylamide; 2-[3-(3-amino-phenylamino)-propenyl]-benzene-1,4-diamine; 2-[3-(4-amino-phenylamino)-propenyl]-benzene-1,4-diamine; 2-(6-methyl-pyridin-2-yl)-benzene-1,4-diamine; 2-pyridin-2-yl-benzene-1,4-diamine; 2-[3-(4-amino-phenylamino)-propenyl]-benzene-1,4-diamine; 2-[3-(3-amino-phenylamino)-propenyl]-benzene-1,4-diamine; 3-(2,5-diamino-phenyl)-N-ethyl-acrylamide: 2-thiazol-2-yl-benzene-1,4-diamine; 4-hydroxy-benzoic acid (2,5-diamino-benzylidene)-hydrazide; 3'-fluoro-biphenyl-2,5-diamine; 2-propenyl-benzene-1,4-diamine; 2'-chloro-biphenyl-2,5-diamine; N-thiophen-3-ylmethyl-benzene-1,4-diamine; N-(3-furylmethyl)benzene-1,4-diamine; 4'-methoxy-biphenyl-2,5-diamine; N-(4-amino-benzyl)-benzene-1,4-diamine; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; biphenyl-2,4,4'-triamine hydrochloride; 5-(4-amino-phenyl)aminomethyl-benzene-1,3-diamine hydrochloride: 5-phenylaminomethyl-benzene-1,3-diamine hydrochloride; 2-[4-amino-2-(3,5-diamino-benzylamino)-phenoxy]-ethanol hydrochloride; 5-(3-amino-phenyl)aminomethyl-benzene-1,3-diamine hydrochloride; N-(2-amino-benzyl)-benzene-1,3-diamine hydrochloride; N-furan-2-ylmethyl-benzene-1,3-diamine hydrochloride; 2-[(3-amino-phenylamino)-methyl]-phenol hydrochloride; 4-amino-2-propylaminomethyl-phenol; N-benzo[1,3]dioxol-5-ylmethyl-benzene-1,3-diamine hydrochloride; N-[4-amino-2-(2-hydroxy-ethyl)-2H-pyrazol-3-yl]-3-(5-amino-2-hydroxy-phenyl)-acrylamide; 4-amino-2-(isopropylaminomethyl)-phenol; 4-thiophen-3-yl-benzene-1,3-diamine; 5-phenylaminomethyl-benzene-1,3-diamine hydrochloride; 5-(3-amino-phenyl)aminomethyl-benzene-1,3-diamine hydrochloride; 4-thiophen-3-yl-benzene-1,3-diamine; 2',4'-diamino-biphenyl-4-ol; 5-cyclobutylamino-2-methyl-phenol; 5-cyclobutylamino-2-methyl-phenol; 4-amino-2-(pyridin-3-ylaminomethyl)-phenol; 5-(3-amino-phenyl)aminomethyl-benzene-1,3-diamine hydrochloride; 5-allylaminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(4-methoxy-benzyl)-benzene-1,3-diamine hydrochloride; N-thiophen-2-ylmethyl-benzene-1,3-diamine hydrochloride; 4-Amino-2-[(2-hydroxy-5-nitro-phenylamino)-methyl]-phenol; 2',4'-diamino-biphenyl-4-ol hydrochloride; biphenyl-2,4,4'-triamine; 5-(4-amino-phenyl)aminomethyl-benzene-1,3-diamine hydrochloride; 2-[4-amino-2-(3,5-diamino-benzylamino)-phenoxy]-ethanol hydrochloride; 5-allylaminomethyl-benzene-1,3-diamine hydrochloride; 5-(3-amino-phenyl)aminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(2-amino-benzyl)-benzene-1,3-diamine hydrochloride; N-(4-methoxy-benzyl)-benzene-1,3-diamine hydrochloride; N-furan-2-ylmethyl-benzene-1,3-diamine hydrochloride; 2-[(3-amino-phenylamino)-methyl]-phenol hydrochloride; N-thiophen-2-ylmethyl-benzene-1,3-diamine hydrochloride; N-benzo[1,3]dioxol-5-ylmethyl-benzene-1,3-diamine hydrochloride; N-[4-amino-2-(2-hydroxy-ethyl)-2H-pyrazol-3-yl]-3-(5-amino-2-hydroxy-phenyl)-acrylamide hydrochloride; 4-amino-2-propylaminomethyl-phenol; 4-amino-2-(isopropylamino-methyl)-phenol hydrochloride; 4-amino-2-[(2-hydroxy-5-nitro-phenylamino)-methyl]-phenol hydrochloride; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; 5-cyclobutylamino-2-methyl-phenol; 4-amino-2-(pyridin-3-ylaminomethyl)-phenol; 5-cyclobutylamino-2-methyl-phenol.

Preferred developers include but are not limited to: p-phenylenediamine derivatives such as: 2-methyl-benzene-1,4-diamine; benzene-1,4-diamine; 1-(2,5-diamino-phenyl)-ethanol; 2-(2,5-diamino-phenyl)-ethanol; 2-(methoxymethyl)benzene-1,4-diamine; N-(2-methoxy-ethyl)benzene-1,4-diamine; 2-[(4-amino-phenyl)-(2-hydroxy-ethyl)-amino]-ethanol; 1-(2,5-diaminophenyl)ethane-1,2-diol; 1-(2'-hydroxyethyl)-2,5-diaminobenzene; 1,3-bis (N-(2-hydroxyethyl)-N-(4-amino-phenyl)amino)-2-propanol; 2,2'-[1,2-ethanediyl-bis-(oxy-2,1-ethanediyloxy)]-bis-benzene-1,4-diamine; N,N-bis(2-hydroxyethyl)-p-phenylenediamine; and mixtures thereof; p-aminophenol derivatives such as: 4-amino-phenol; 4-methylamino-phenol; 4-amino-3-methyl-phenol; 4-amino-2-methoxymethyl-phenol; 1-(5-amino-2-hydroxy-phenyl)-ethane-1,2-diol; 4-amino-2-aminomethylphenol; 4-amino-1-hydroxy-2-(2'-hydroxyethylaminomethyl)benzene; 5-aminosalicylic acid and salts thereof, and mixtures thereof; o-phenylenediamine derivatives such as: 3,4-Diaminobenzoic acid and salts thereof; o-aminophenol derivatives such as: 2-amino-phenol; 2-amino-5-methyl-phenol; 2-amino-6- methyl-phenol; N-(4-amino-3-hydroxy-phenyl)-acetamide; 2-amino-4-methyl-phenol; 2-amino-5-ethyl-phenol; and mixtures thereof; and heterocyclic derivatives such as: pyrimidine-2,4,5,6-tetramine: 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-dimethyl-pyridine-2,5-diamine; 4-Hydroxy-2,5,6-triaminopyrimidine: and mixtures thereof.

More preferred developers include: 2-methyl-benzene-1,4-diamine; 2-(methoxymethyl)benzene-1,4-diamine; benzene-1,4-diamine; N,N-bis(2-hydroxyethyl)-p-phenylenediamine; 4-amino-phenol; 4-methylamino-phenol; 4-amino-3-methyl-phenol; 2-amino-phenol; 2-amino-5-methyl-phenol; 2-amino-5-ethyl-phenol; 2-amino-6-methyl-phenol; 1-methyl-1H-pyrazole-4,5-diamine; 2-(4,5-diamino-1H-pyrazol-1-yl)ethanol; 2,5-diaminotoluene; 2,5-diaminophenylethyl alcohol; and mixtures thereof.

C. Couplers

Suitable couplers for use in the compositions described herein include, but are not limited to: phenols, resorcinols, naphthols, m-aminophenols, m-phenylenediamines, and heterocyclic compounds, and derivatives thereof such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; 7-amino-4-hydroxy-naphthalene-2-sulfonic acid; 2-isopropyl-5-methylphenol; 1,2,3,4-tetrahydro-naphthalene-1,5-diol; 2-chloro-benzene-1,3-diol; 4-hydroxy-naphthalene-1-sulfonic acid; benzene-1,2,3-triol; naphthalene-2,3-diol; 5-dichloro-2-methylbenzene-1,3-diol; 4,6-dichlorobenzene-1,3-diol; 2,3-dihydroxy-[1,4]naphthoquinone; and 1-Acetoxy-2-methylnaphthalene; m-phenylenediamines such as: 2,4-diaminophenol; benzene-1,3-diamine; 2-(2,4-diaminophenoxy)-ethanol; 2-[(3-amino-phenyl)-(2-hydroxy-ethyl)-amino]-ethanol; 2-methyl-benzene-1,3-diamine; 2-[[2-(2,4-diamino-phenoxy)-ethyl]-(2-hydroxy-ethyl)-amino]-ethanol; 4-{3-[(2,4-diaminophenyl)oxy]propoxy}benzene-1,3-diamine; 2-(2,4-diamino-phenyl)-ethanol; 2-(3-amino-4-methoxy-phenylamino)-ethanol; 4-(2-amino-ethoxy)-benzene-1,3-diamine; (2,4-diamino-phenoxy)-acetic acid; 2-[2,4-diamino-5-(2-hydroxy-ethoxy)-phenoxy]-ethanol; 4-ethoxy-6-methyl-benzene-1,3-diamine; 2-(2,4-diamino-5-methyl-phenoxy)-ethanol; 4,6-dimethoxy-benzene-1,3-diamine; 2-[3-(2-hydroxy-ethylamino)-2-methyl-phenylamino]-ethanol; 3-(2,4-diamino-phenoxy)-propan-1-ol; N-[3-(dimethylamino)phenyl]urea; 4-methoxy-6-methyl-benzene-1,3-diamine; 4-fluoro-6-methylbenzene-1,3-diamine; 2-({3-[(2-hydroxyethyl)amino]-4,6-dimethoxyphenyl}-amino)ethanol; 3-(2,4-diaminophenoxy)-propane-1,2-diol; 2-[2-amino-4-(methylamino)-phenoxy]ethanol; 2-[(5-amino-2-ethoxy-phenyl)-(2-hydroxy-ethyl)-amino]-ethanol; 2-[(3-aminophenyl)amino]ethanol; 2,4-Diamino-5-(2'-hydroxyethyloxy)toluene; N,N-Dimethyl-3-ureidoaniline; N-(2-aminoethyl)benzene-1,3-diamine; 4-{[(2,4-diaminophenyl)oxy]methoxy}-benzene-1,3-diamine; 1-methyl-2,6-bis(2-hydroxyethylamino)benzene; and 2,4-dimethoxybenzene-1,3-diamine; m-aminophenols such as: 3-amino-phenol; 2-(3-hydroxy-4-methyl-phenylamino)-acetamide; 2-(3-hydroxy-phenylamino)-acetamide; 5-amino-2-methyl-phenol; 3-amino-2,6-dimethylphenol; 5-(2-hydroxy-ethylamino)-2-methyl-phenol; 5-amino-2,4-dichloro-phenol; 3-amino-2-methyl-phenol; 3-amino-2,6-dimethyl-phenol; 3-amino-2-chloro-6-methyl-phenol; 5-amino-2-(2-hydroxy-ethoxy)-phenol; 2-chloro-5-(2,2,2-trifluoro-ethylamino)-phenol; 5-amino-4-chloro-2-methyl-phenol; 3-cyclopentylamino-phenol; 5-[(2-hydroxyethyl)amino]-4-methoxy-2-methylphenol; 5-amino-4-methoxy-2-methylphenol; 3-(dimethylamino)phenol; 3-(diethylamino)phenol; 5-amino-4-fluoro-2-methylphenol; 5-amino-4-ethoxy-2-methylphenol; 3-amino-2,4-dichloro-phenol; 3-[(2-methoxyethyl)amino]phenol; 3-[(2-hydroxyethyl)amino]phenol; 5-amino-2-ethyl-phenol; 5-amino-2-methoxyphenol; 5-[(3-hydroxy-propyl)amino]-2-methylphenol; 3-[(3-hydroxy-2-methylphenyl)-amino]propane-1,2-diol; 3-[(2-hydroxyethyl)amino]-2-methylphenol; 1-methyl-2-hydroxy-4-(2'-hydroxyethyl)amino-benzene; 1,3-bis-(2,4-diaminophenoxy)propane; and heterocyclic derivatives such as: 3,4-dihydro-2H-1,4-benzoxazin-6-ol; 6-methoxyquinolin-8-amine; 4-methylpyridine-2,6-diol; 2,3-dihydro-1,4-benzodioxin-5-ol; 1,3-benzodioxol-5-ol; 2-(1,3-benzodioxol-5-ylamino)ethanol; 3,4-dimethylpyridine-2,6-diol; 5-chloropyridine-2,3-diol; 2,6-dimethoxypyridine-3,5-diamine; 1,3-benzodioxol-5-amine; 2-{[3,5-diamino-6-(2-hydroxy-ethoxy)-pyridin-2-yl]oxy}-ethanol; 1H-indol-4-ol; 5-amino-2,6-dimethoxypyridin-3-ol; 1H-indole-5,6-diol; 1H-indol-7-ol; 1H-indol-5-ol; 1H-indol-6-ol; 6-bromo-1,3-benzodioxol-5-ol; 2-aminopyridin-3-ol; pyridine-2,6-diamine; 3-[(3,5-diaminopyridin-2-yl)oxy]propane-1,2-diol; 5-[(3,5-diaminopyridin-2-yl)oxy]pentane-1,3-diol; indoline-5,6-diol; 3,5-dimethoxypyridine-2',6-diamine; 6-methoxypyridine-2,3-diamine; 3,4-dihydro-2H-1,4-benzoxazin-6-amine; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 5-methylpyrazolo[5,1-e]-1,2,3-triazole; 5-methyl-6-chloropyrazolo[5,1-e]-1,2,3-triazole; 5-phenylpyrazolo[5,1-e]-1,2,3-triazole and its addition salts; 1H-2,6-dimethylpyrazolo[1,5-b]-1,2,4-triazole tosylate; 7,8-dicyano-4-methylimidazolo-[3,2-a]imidazole; 2,7-dimethylpyrazolo[1,5-a]pyrimidin-5-one; 2,5-dimethylpyrazolo[1,5-a]pyrimidin-7-one; and 2-methyl-5-methoxymethyl-pyrazolo[1,5-a]pyrimidin-7-one;
6-hydroxybenzomorpholine; and 3-amino-2-methylamino-6-methoxypyridine; and mixtures thereof.

Preferred couplers include but are not limited to: phenol, resorcinol, and naphthol derivatives such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; and 2-isopropyl-5-methylphenol; 1,2,4-trihydroxybenzene; 1-acetoxy-2-methylnaphthalene; and mixtures thereof; m-phenylenediamine derivatives such as: benzene-1,3-diamine; 2-(2,4-diamino-phenoxy)-ethanol; 4-{3-[(2,4-diaminophenyl)oxy] propoxy}benzene-1,3-diamine; 2-(3-amino-4-methoxy-phenylamino)-ethanol; 2-[2,4-diamino-5-(2-hydroxy-ethoxy)-phenoxy]-ethanol; and 3-(2,4-diamino-phenoxy)-propan-1-ol; 2,4-diamino-5-(2'-hydroxyethyloxy)toluene; N,N-dimethyl-3-ureidoaniline; 2,4-diamino-5-fluorotoluene; 1-methyl-2,6-bis(2-hydroxyethylamino)benzene; and mixtures thereof; m-aminophenol derivatives such as: 3-aminophenol; 5-amino-2-methyl-phenol; 3-amino-2,6-dimethylphenol; 5-(2-hydroxy-ethylamino)-2-methyl-phenol; and 3-amino-2-methyl-phenol; 1-hydroxy-3-amino-2,4-dichlorobenzene; 1,3-bis-(2,4-diaminophenoxy)propane; 1-hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol; 1,3-benzodioxol-5-ol; 1,3-benzodioxol-5-amine; 1H-indol-4-ol; 1H-indole-5,6-diol; 1H-indol-7-ol; 1H-indol-5-ol; 1H-indol-6-ol; pyridine-2,6-diamine; 2-aminopyridin-3-ol; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,24-triazole; 6-methylpyrazolo-[1,5-a]benzimidazole; 2,6-dihydroxypyridine; 2,6-dihydroxy-3,4-dimethylpyridine; 6-hydroxybenzomorpholine; 2,6-dihydroxy-3,4-dimethylpyridine; 3,5-diamino-2,6-dimethoxypyridine; 3-amino-2-methylamino-6-methoxypyridine; and mixtures thereof.

More preferred couplers include: 2-amino-5-ethyl-phenol; benzene-1,3-diol; 4-chlorobenzene-1,3-diol; 4,6-dichlorobenzene-1,3-diol; 2-methyl-benzene-1,3-diol; 2-amino-4-(2'-hydroxyethyl)aminoanisole; 2,4-diaminobenzyl alcohol; 2,4-diaminophenylethyl alcohol; m-phenylenediamine; 5-amino-2-methyl-phenol; 3-amino-2,6-dimethylphenol; 2,4-diaminophenoxyethanol; 4-amino-2-hydroxyphenoxyethanol; 1-naphthol; 2-methyl-naphthol; 3-aminophenol; 3-amino-2-methylphenol; 4-hydroxy-1,2-methylenedioxybenzene; 4-amino-1,2-methylenedioxbenzene; 4-(2'-hydroxyethyl)amino-1,2-methylenedioxybenzene; 1-Methyl-2-hydroxy-4-(2'-hydroxyethyl)aminobenzene; 2,4-diaminophenetole; 2,4-diamino-5-methylphenetole; 4-hydroxyindole; 3-amino-5-hydroxy-2,6-dimethoxypyridine; and 3,5-diamino-2,6-dimethoxypyridine; benzene-1,3-diamine; 2-aminopyridin-3-ol; 1-phenyl-3-methylpyrazol-5-one; and mixtures thereof.

Additional preferred developers and couplers include 5-methoxymethyl-2-aminophenol; 5-ethyl-2-aminophenol; 5-phenyl-2-aminophenol; and 5-cyanoethyl-2-aminophenol.

Any of the developers and couplers described above may be combined to form a mixture of developers and couplers. The hair dye compositions of the present invention will generally comprise from about 0.001% to about 10% by weight of the dyeing composition of developer and coupler dyes. For example, compositions providing low intensity dyeing such as natural blond to light brown hair shades generally comprise from about 0.001% to about 5%, preferably from about 0.1% to about 2%, more preferably from about 0.2% to about 1% by weight of dyeing composition of developers and couplers. Darker shades such as browns and black typically comprise from about 0.001% to about 10% by weight, preferably from about 0.05% to about 7% by weight, more preferably form about 1% to about 5% of developers and couplers. Developer compounds are generally used in approximately equimolar quantities with respect to coupler compounds. The developer compound may, however, be present in a greater or lesser quantity with respect to the coupler compound.

D. Direct Dyes

The inventive compositions may also comprise compatible direct dyes, in an amount sufficient to provide additional coloring, particularly with regard to intensity. Typically, such an amount will range from about 0.05% to about 4%, by weight of the dye composition. Suitable direct dyes include but are not limited to: Acid Yellow 1; Acid Orange 3; Disperse Red 17; Basic Brown 17; Acid Black 52; Acid Black 1; Disperse Violet 4; 4-nitro-o-phenylenediamine; 2-nitro-p-phenylenediamine; Picramic Acid; HC Red No. 13; 1,4-bis-(2'-hydroxyethyl)-amino-2-nitrobenzene; HC Yellow No. 5; HC Red No. 7; HC Blue No. 2; HC Yellow No. 4; HC Yellow No. 2; HC Orange No. 1; HC Red No. 1; 2-chloro-5-nitro-N-hydroxyethyl-p-phenylenediamine; HC Red No. 3; 4-amino-3-nitrophenol; 2-hydroxyethylamino-5-nitroanisole; 3-nitro-p-hydroxyethylaminophenol; 2-amino-3-nitrophenol; 6-nitro-o-toluidine; 3-methylamino-4-nitrophenoxyethanol; 2-nitro-5-glycerylmethylaniline; HC Yellow No. 11; HC Violet No. 1; HC Orange No. 2; HC Orange No. 3; HC Yellow No. 9; 4-nitrophenyl aminoethylurea; HC Red No. 10; HC Red No. 11; 2-hydroxyethyl picramic acid; HC Blue No. 12; HC Yellow No. 6: hydroxyethyl-2-nitro-p-toluidine; HC Yellow No. 12; HC Blue No. 10; HC Yellow No. 7; HC Yellow No. 10; HC Blue No. 9; N-ethyl-3-nitro PABA; 4-amino-2-nitrophenyl-amine-2'-carboxylic acid; 2-chloro-6-ethylamino-4-nitrophenol; 6-nitro-2,5-pyridinediamine; HC Violet No. 2; 2-amino-6-chloro-4-nitrophenol; 4-hydroxypropylamino-3-nitrophenol; HC Yellow No. 13; 1,2,3,4-tetrahydro-6-nitrochinoxalin; HC Red No. 14; HC Yellow No. 15; HC Yellow No. 14; 3-amino-6-methylamino-2-nitropyridine; 2,6-diamino-3-((pyridine-3-yl)azo)pyridine; Basic Red No. 118: Basic Orange No. 69; N-(2-nitro-4-aminophenyl)-allylamine: 4-[(4-amino-3-methylphenyl)(4-imino-3-methyl-2,5-cyclohexadien-1-ylidene) methyl]-2-methyl-benzeneamine-hydrochloride; 2-[[4-(dimethyl-amino)phenyl]azo]-1,3-dimethyl-1H-imidazolium chloride; 1-methyl-4-[(methylphenyl-hydrazono)methyl]-pyridinium, methyl sulfate; 2-[(4-aminophenyl)azo]-3-dimethyl-1H-imidazolium chloride; Basic Red 22; Basic Red 76; Basic Brown 16; Basic Yellow 57; 7-(2',4'-dimethyl-5'-sulfophenylazo)-5-sulfo-8-hydroxynaphthalene; Acid Orange 7; Acid Red 33; 1-(3'-nitro-5'-sulfo-6'-oxophenylazo)-oxo-naphthalene chromium complex; Acid Yellow 23; Acid Blue 9; Basic Violet 14; Basic Blue 7; Basic Blue 26; sodium salt of mixture of mono- & disulfonic acids (mainly the latter) of quinophthlanone or 2-quinolylindandione; Basic Red 2; Basic Blue 99; Disperse Red 15; Acid Violet 43; Disperse Violet 1; Acid Blue 62; Pigment Blue 15; Acid Black 132; Basic Yellow 29; Disperse Black 9; 1-(N-methylmorpholinium-propylamino)-4-hydroxy-anthraquinone methylsulfate; HC Blue No. 8; HC Red No. 8; HC Green No. 1; HC Red No. 9; 2-hydroxy-1,4-naphthoquinone; Acid Blue 199; Acid Blue 25; Acid Red 4; Henna Red; Indigo; Cochenille; HC Blue No. 14; Disperse Blue 23; Disperse Blue 3; Disperse Blue 377; Basic Red 51; Basic Orange 31; Basic Yellow 87; and mixtures thereof. Preferred direct dyes include but are not limited to: Disperse Black 9; HC Yellow 2; HC Yellow 4; HC Yellow 15; 4-nitro-o-phenylenediamine; 2-amino-6-chloro-4-nitrophenol; HC Red 3; Disperse Violet 1; HC Blue 2; Disperse Blue 3; Disperse Blue 377; Basic Red 51; Basic Orange 31; Basic Yellow 87; and mixtures thereof.

E. Oxidizing Agent

The inventive compositions may comprise an oxidizing agent, present in an amount sufficient to bleach melanin pigment in hair and/or cause formation of dye chromophores from oxidative dye precursors (including developers and/or couplers when present). Typically, such an amount ranges from about 1% to about 20%, preferably from about 3% to about 15%, more preferably from about 6% to about 12%, by weight of the oxidizing composition (the oxidizing composition is separate from the dye composition, which contains the developers and couplers). Inorganic peroxygen materials capable of yielding hydrogen peroxide in an aqueous medium are preferred and include but are not limited to: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, preferably sodium salts thereof), which may be incorporated as monohydrates, tetrahydrates, etc.; alkali metal bromates; enzymes; and mixtures thereof. Preferred is hydrogen peroxide.

F. Thickeners

The inventive compositions may comprise a thickener in an amount sufficient to provide the composition with a viscosity so that it can be readily applied to the hair without unduly dripping off the hair and causing mess. Typically, such an amount will be at least about 0.1%, preferably at least about 0.5%, more preferably, at least about 1%, by weight of the composition.

Preferred for use herein are salt tolerant thickeners, including but not limited to: xanthan, guar, hydroxypropyl guar, scleroglucan, methyl cellulose, ethyl cellulose (available as Aquacote™), hydroxyethyl cellulose (Natrosol™), carboxymethyl cellulose, hydroxypropylmethyl cellulose, microcrystalline cellulose, hydroxybutylmethyl cellulose, hydroxypropyl cellulose (available as Klucel™), hydroxyethyl ethyl cellulose, cetyl hydroxyethyl cellulose (available as Natrosol™ Plus 330), N-vinylpyrollidone (available as Povidone™), Acrylates/Ceteth-20 Itaconate Copolymer (available as Structure™ 3001), hydroxypropyl starch phosphate (available as Structure™ ZEA), polyethoxylated urethanes or polycarbamyl polyglycol ester (e.g. PEG-150/Decyl/SMDI copolymer (available as Aculyn™ 44), PEG-150/Stearyl/SMDI copolymer (available as Aculyn™ 46), trihydroxystearin (available as Thixcin™), acrylates copolymer (e.g. available as Aculyn™ 33) or hydrophobically modified acrylate copolymers (e.g. Acrylates/Steareth-20 Methacrylate Copolymer (available as Aculyn™ 22), non-ionic amphophilic polymers comprising at least one fatty chain and at least one hydrophilic unit selected from polyether urethanes comprising at least one fatty chain, and blends of Ceteth-10 phosphate, Di-cetyl phosphate and Cetearyl alcohol (available as Crodafos™ CES).

G. Chelants

The inventive compositions may comprise chelants in an amount sufficient to reduce the amount of metals available to interact with formulation components, particularly oxidizing agents, more particularly peroxides. Typically such an amount will range from at least 0.25%, preferably at least 0.5%, by weight of the composition. Suitable chelants for use herein include but are not limited to: diamine-N,N'-dipolyacid, monoamine monoamide-N,N'-dipolyacid, and N,N'-bis (2-hydroxybenzyl)ethylenediamine-N,N'-diacetic acid chelants (preferably EDDS (ethylenediaminedisuccinic acid)), carboxylic acids (preferably aminocarboxylic acids), phosphonic acids (preferably aminophosphonic acids) and polyphosphoric acids (in particular straight polyphosphoric acids), their salts and derivatives.

H. pH Modifiers and Buffering Agents

The inventive compositions may farther comprise a pH modifier and/or buffering agent in an amount that is sufficiently effective to adjust the pH of the composition to fall within a range from 3 to 13, preferably from 8 to 12, more preferably from 9 to 11. Suitable pH modifiers and/or buffering agents for use herein include, but are not limited to: ammonia, alkanolamines such as monoethanolamine, diethanolamine, triethanolamine, monopropanolamine, dipropanolamine, tripropanolamine, 2-amino-2-methyl-1-propanol, and 2-amino-2-hydroxymethyl-1,3,-propandiol and guanidium salts, alkali metal and ammonium hydroxides and carbonates, preferably sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

I. Carbonate Ion Source

The inventive compositions may comprise a source of carbonate ions, carbamate ions and or hydrocarbonate ions, in a sufficient amount to reduce damage to the hair during the coloring process. Typically, such an amount will range from about 0.1% to about 15%, preferably about 0.1% to about 10%, more preferably about 1% to about 7%, by weight of the composition. Suitable sources for the ions include but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Preferred sources of carbonate ions are sodium hydrogen carbonate and potassium hydrogen carbonate. Also preferred are ammonium carbonate and ammonium hydrogen carbonate.

J. Radical Scavenger

The inventive compositions may comprise a radical scavenger, in a sufficient amount to reduce damage to the hair during the coloring process. Typically, such an amount will range from about 0.1% to about 10%, preferably from about 1% to about 7%, by weight of the composition. The radical scavenger is preferably selected such that it is not an identical species as the alkalizing agent. When the inventive compositions contain both a radical scavenger and a source of carbonate ions, the radical scavenger is preferably present at an amount such that the ratio of radical scavenger to carbonate ion is from 1:1 to 1:4. The radical scavenger is a species that can react with a carbonate radical to convert the carbonate radical by a series of fast reactions to a less reactive species. Preferably, when the radical scavenger comprises an N atom, it has a $pKa>7$ to prevent the protonation of the nitrogen. Preferred radical scavengers may be selected from the classes of alkanolamines, amino sugars, amino acids and mixtures thereof, and may include, but are not limited to: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other preferred radical scavenger compounds include benzylamine, glutamic acid, imidazole, di-tert-butylhydroxytoluene, hydroquinone, catechol and mixtures thereof.

III. Methods of Manufacture

The compounds of this invention may be obtained using conventional methods. A general description of how to make the compounds is provided above and specific examples are provided below. The compositions of this invention may also be obtained using conventional methods. The keratin dyeing compositions may be formed as solutions, preferably as aqueous or aqueous-alcohol solutions. The hair dye product compositions may preferably be formed as thick liquids, creams, gels, or emulsions, which are a mixture of the dye compound, other dye ingredients, and conventional cosmetic additive ingredients suitable for the particular preparation.

IV. Methods of Use

The inventive keratin dyeing compositions may be used by admixing them with a suitable oxidant, which reacts with the oxidative dye precursors to develop the hair dye product composition. The oxidant is usually provided in an aqueous composition, i.e., an oxidizing composition, which is normally provided as a separate component of the finished keratin dyeing product system and present in a separate container.

The mixed dye/oxidizing composition, as it is applied to the hair, can be weakly acidic, neutral or alkaline, typically having a pH from 6 to 11, preferably from 7 to 10, more preferably from 8 to 10. The pH of the oxidizing composition is typically acidic, and generally the pH is from 2.5 to 6.5, preferably from 3 to 5. The pH of the hair compositions may be adjusted using a pH1 modifier as mentioned above.

In use, the dye composition and the oxidizing composition are mixed immediately prior to use and a sufficient amount of the mixture is applied to the hair, according to the hair abundance, generally from 60 to 200 grams. The mixture remains in contact with the hair for an amount of time effective to dye the hair. Typically, the mixture is allowed to act on the hair for about 2 to about 60, preferably about 15 to about 45, more preferably, about 30 minutes, at a temperature ranging from about 15° to about 50° C. Thereafter, the hair is rinsed with water, to remove the colorant mixture, and dried. Optionally, a separate conditioning product may also be provided.

Together, components of the keratin dyeing composition form a system for dyeing hair. This system may be provided as a kit comprising in a single package separate containers of the keratin dyeing composition components or other hair treatment product, and instructions for use.

EXAMPLES

The following are non-limiting examples of the dye compositions. The examples are given solely for the purpose of illustration and are not to be construed as limitations of the dye compositions, as many variations thereof are possible without departing from the spirit and scope of the invention, which would be recognized by one of ordinary skill in the art. In the examples, all concentrations are listed as weight percent, unless otherwise specified.

The following compositions can be used for dyeing hair. The dyeing composition is mixed with an equal weight of a 20-volume hydrogen peroxide solution (6% by weight). The resulting mixture is applied to the hair and permitted to remain in contact with the hair for 10-30 minutes. This dyed hair is then shampooed and rinsed with water and dried.

Common Bases For Dyeing—

| Common Base A - Ingredients | Weight (g) | Common Base B - Ingredients | Weight (g) |
|---|---|---|---|
| Propylene glycol | 9.5 | Propylene glycol | 6.0 |
| Ammonium hydroxide | 5 | Ammonium carbonate | 10.0 |
| Ethoxydiglycol | 4 | Glycine | 3.86 |
| Ethanolamine | 4.5 | Cetearyl alcohol | 4.5 |
| Oleic acid | 1 | Sodium hydroxide | 2.25 |
| Hexylene glycol | 6 | Ceteth-10 Phosphate | 4.5 |
| Cocamidopropyl betaine | 3.5 | Dicetyl phosphate | 4.5 |
| Oleth-10 | 0.3 | Xanthan gum | 0.08 |
| Oleth-2 | 0.3 | Erythorbic acid | 0.4 |
| Dilinoleic acid | 1.5 | EDTA | 0.05 |
| C12-C15 Pareth-3 | 0.5 | Sodium sulfite | 0.1 |
| Soytrimonium chloride | 7 | | |
| Sodium metasilicate | 0.05 | | |
| Erythorbic acid | 0.5 | | |
| EDTA | 0.03 | | |
| Sodium sulfite | 0.3 | | |
| 1-Phenyl-3-methyl-5-pyrazolone | 0.2 | | |

| Ingredients | 1 | 2 | 3 | 4 | 5 | 6 | 7 |
|---|---|---|---|---|---|---|---|
| 2-(4,5-diamino-3-methoxy-1H-pyrazol-1-yl)ethanol | 0.05 | 0.04 | 0.03 | 0.01 | 0.05 | 0.15 | 0.2 |
| 2-methylbenzene-1,4-diamine | 0.05 | 0.06 | 1.20 | 0.70 | 0.20 | 1.50 | 0.30 |
| N,N-Bis(2-hydroxyetyl)-p-phenylendiamine | 0.1 | | | | | | 0.02 |
| 4-Aminophenol | 0.2 | 0.02 | 0.3 | | 0.2 | 0.4 | |
| 4-Amino-3-methylphenol | | | | 0.4 | | | 0.2 |
| 3-Aminophenol | 0.1 | | | | | | |
| 5-Amino-2-methylphenol | | 0.02 | 0.02 | | 0.02 | | 0.04 |
| 1-Naphthol | 0.05 | | | | | | |
| Resorcinol | 0.15 | 0.1 | 0.1 | 0.4 | 0.1 | 0.5 | 0.4 |
| 2-Methylresorcinol | | | 0.4 | | | | |
| 1-Hydroxyethyl-4,5-diaminopyrazole | | | | | | 0.2 | |
| Common base A | 44.18 | 44.18 | 44.18 | 44.18 | 44.18 | 44.18 | 44.18 |
| Water | qs | qs | qs | qs | qs | qs | qs |

| Ingredients | 8 | 9 | 10 | 11 | 12 | 13 | 14 | 15 |
|---|---|---|---|---|---|---|---|---|
| 4,5-diamino-1-hexyl-1H-pyrazole-3-carbonitrile | 0.3 | 0.2 | 0.2 | 0.1 | 0.1 | 0.2 | 0.6 | |
| 4,5-diamino-1-methyl-1H-pyrazole-3-carbonitrile | | | | | | | | 0.59 |
| 2-(methoxymethyl)benzene-1,4-diamine | 1.25 | 0.50 | 0.01 | 0.95 | 0.05 | 0.55 | 0.90 | |
| N,N-Bis(2-hydroxyetyl)-p-phenylendiamine | 0.33 | 0.02 | | | | | | |
| 4-Aminophenol | 0.5 | | 0.7 | | 0.9 | 1.2 | 0.3 | |
| 4-Amino-2-methylphenol | | 1 | | 1.2 | | | | |
| 3-Aminophenol | 0.3 | | | | | | | |

-continued

| Ingredients | | | | | | | |
|---|---|---|---|---|---|---|---|
| 3-Amino-2,6-dimethylphenol | | | | | | | 0.34 |
| 5-Amino-2-methylphenol | | 0.4 | 0.4 | 2.5 | 2.5 | 1 | 0.8 |
| 1-Naphthol | | | | | | | |
| Resorcinol | 0.3 | 0.1 | 0.1 | 0.1 | 0.1 | 0.6 | 0.1 |
| 2-Methylresorcinol | 0.4 | 0.6 | 0.6 | | | | |
| 1-Hydroxyethyl-4,5-diaminopyrazole | | | | 0.2 | 0.2 | 0.4 | |
| Common Base A | 44.18 | 44.18 | 44.18 | 44.18 | 44.18 | 44.18 | 44.18 |
| Water | qs | qs | qs | qs | qs | qs | qs |

| Ingredients | 16 | 17 | 18 | 19 | 20 | 21 | 22 |
|---|---|---|---|---|---|---|---|
| 3-chloro-1-(pyridin-2-yl-1H-pyrazole-4,5-diamine | 1 | 0.1 | 0.5 | 0.5 | 0.1 | 0.1 | 0.5 |
| 2-(methoxymethyl)benzene-1,4-diamine | | 1.25 | 0.50 | 0.01 | 0.95 | 0.05 | 0.55 | 0.90 |
| N,N-Bis(2-hydroxyetyl)-p-phenylendiamine | | | | | | | 0.1 |
| 4-Aminophenol | | 0.4 | | | | 0.8 | 0.1 |
| 4-Amino-2-methylphenol | | | 0.6 | | | 0.8 | |
| 3-Aminophenol | | | | 1.5 | 1 | | 0.1 |
| 5-Amino-2-methylphenol | | 1.4 | 0.5 | | | 0.1 | 0.1 |
| 1-Naphthol | | | | | 0.1 | 0.1 | 0.1 |
| Resorcinol | | | 0.5 | | 0.2 | 0.2 | 0.5 |
| 2-Methylresorcinol | | | | | 0.5 | 0.8 | 0.1 |
| 1-Hydroxyethyl-4,5-diaminopyrazole | | | 0.6 | 2 | 1.5 | | |
| Common Base B | 44.18 | 44.18 | 44.18 | 44.18 | 44.18 | 44.18 | 44.18 |
| Water | qs | qs | qs | qs | qs | qs | qs |

| Ingredients | 23 | 24 | 25 | 26 | 27 | 28 | 29 |
|---|---|---|---|---|---|---|---|
| 3-cyano-1-(4-methoxybenzyl)-1H-pyrazol-4,5-diamine | 0.3 | 0.5 | 0.4 | 0.3 | 0.08 | 1.30 | 0.80 |
| Dibenzo[b,d]furan-1,3-diol | | | | | 0.5 | 0.4 | 0.3 |
| N,N-Bis(2-hydroxyetyl)-p-phenylendiamine | 0.1 | 0.1 | 0.3 | | 0.1 | 0.3 | |
| p-Phenylenediamine | | | | 0.4 | | | 0.4 |
| 4-Aminophenol | 0.5 | | 0.1 | 0.2 | | 0.1 | 0.2 |
| 4-Amino-2-methylphenol | | 1 | | | 1 | | |
| 3-Aminophenyl | 0.3 | | 0.2 | | | 0.2 | |
| 5-Amino-2-methylphenol | | 0.4 | 0.2 | 0.5 | 0.4 | 0.2 | 0.5 |
| 1-Naphthol | | | 0.1 | | | 0.1 | |
| Resorcinol | 0.3 | 0.2 | 0.4 | 0.3 | 0.2 | 0.4 | 0.3 |
| 2-Methylresorcinol | 0.4 | 0.2 | | | 0.2 | | |
| 1-Hydroxyethyl-4,5-diaminopyrazole | | 0.5 | 0.1 | 0.3 | 0.5 | 0.1 | 0.3 |
| Common Base B | 44.18 | 44.18 | 44.18 | 44.18 | 44.18 | 44.18 | 44.18 |
| Water | qs | qs | qs | qs | qs | qs | qs |

| Ingredients | 30 | 31 | 32 | 33 | 34 | 35 | 36 |
|---|---|---|---|---|---|---|---|
| 3-methoxy-1-p-tolyl-1H-pyrazole-4,5-diamine | | 0.5 | 0.4 | 0.3 | | | |
| 9H-Carbazole-2,7-diol | | | | | 0.5 | 0.4 | 0.3 |
| N,N-Bis(2-hydroxyetyl)-p-phenylendiamine | 0.1 | 0.1 | 0.3 | | 0.1 | 0.3 | |
| p-Phenylenediamine | | | | 0.4 | | | 0.4 |
| 4-Aminophenol | 0.5 | | 0.1 | 0.2 | | 0.1 | 0.2 |
| 4-Amino-2-methylphenol | | 1 | | | 1 | | |
| 3-Aminophenol | 0.3 | | 0.2 | | | 0.2 | |
| 5-Amino-2-methylphenol | | 0.4 | 0.2 | 0.5 | 0.4 | 0.2 | 0.5 |
| 1-Naphthol | | | 0.1 | | | 0.1 | |

-continued

| | | | | | | | |
|---|---|---|---|---|---|---|---|
| Resorcinol | 0.3 | 0.2 | 0.4 | 0.3 | 0.2 | 0.4 | 0.3 |
| 2-Methylresorcinol | 0.4 | 0.2 | | | 0.2 | | |
| 1-Hydroxyethyl-4,5-diaminopyrazole | | 0.5 | 0.1 | 0.3 | 0.5 | 0.1 | 0.3 |
| Common Base B | 44.18 | 44.18 | 44.18 | 44.18 | 44.18 | 44.18 | 44.18 |
| Water | qs | qs | qs | qs | qs | qs | qs |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound selected from the group consisting of 4,5-diamino-1-methyl-1H-pyrazole-3-carbonitrile; 3-methoxy-1-propyl-1H-pyrazole-4,5-diamine; 3-methoxy-1-(2-methoxyethyl)-1H-pyrazole-4,5-diamine; 1-(2-aminoethyl)-3-methoxy-1H-pyrazole-4,5-diamine; 3-bromo-1-(2-hydroxyethyl)-1H-pyrazol-4,5-diamine; 8-methoxy-1,2,4,5-tetrahydropyrazolo[5,1-d][1,3,5]oxadiazepin-9-amine; 1-benzyl-3-(ethylthio)-$N^5,N^5$-dimethyl-1H-pyrazole-4,5-diamine; 1-methyl-3-phenoxy-1H-pyrazole-4,5-diamine; 1-(2-hydroxyethyl)-3-methoxy-1H-pyrazol-4,5-diamine; 1-cyclohexyl-3-methoxy-1H-pyrazole-4,5-diamine; 6-methoxy-1-methyl-2,3-dihydro-1H-imidazo[1,2-b]pyrazol-7-amine; 2-methoxy-4,5,6,7-tetrahydropyrazolo[1,5-a]pyrimidin-3-amine; 3-methoxy-1-(2-(methylamino)ethyl)-1H-pyrazole-4,5-diamine; 3-methoxy-1-octyl-1H-pyrazole-4,5-diamine; 3-methoxy-1-pentyl-1H-pyrazole-4,5-diamine; 1-(3-amino-2-hydroxypropyl)-3-methoxy-1H-pyrazol-4,5-diamine; 6-methoxy-2,3-dihydro-1H-imidazo[1,2-b]pyrazol-7-amine; 6-ethoxy-2,3-dihydro-1H-imidazo[1,2-b]pyrazol-7-amine; 3-methoxy-1-(2-(pyrrolidin-1-yl)ethyl)-1H-pyrazole-4,5-diamine; 1-(3-aminopropyl)-3-methoxy-1H-pyrazole-4,5-diamine; 3-methoxy-$N^5,N^5$-dimethyl-1-propyl-1H-pyrazole-4,5-diamine; 1-hexyl-3-methoxy-1H-pyrazole-4,5-diamine; 1-butyl-3-methoxy-1H-pyrazole-4,5-diamine; 5-(4,5-diamino-3-methoxy-1H-pyrazol-1-yl)pentan-1-ol; 3-methoxy-1-propyl-5-(pyrrolidin-1-yl)-1H-pyrazol-4-amine; 1-hexyl-3-methoxy-$N^5$-methyl-1H-pyrazole-4,5-diamine; 1-isopropyl-3-methoxy-1H-pyrazole-4,5-diamine; 1-ethyl-3-methoxy-1H-pyrazole-4,5-diamine; 1-(2,3-dihydroxypropyl)-3-methoxy-1H-pyrazol-4,5-diamine; 1-hexyl-3-methoxy-$N^5,N^5$-dimethyl-1H-pyrazole-4,5-diamine; 3-methoxy-1-(4-methoxybenzyl)-1H-pyrazole-4,5-diamine; 3-methoxy-1-(pyridin-2-yl)-1H-pyrazole-4,5-diamine; 3-methoxy-1-phenyl-1H-pyrazole-4,5-diamine; 3-methoxy-1-(pyrimidin-2-yl)-1H-pyrazole-4,5-diamine; 1-(4-ethylphenyl)-3-methoxy-1H-pyrazole-4,5-diamine; 3-methoxy-1-p-tolyl-1H-pyrazole-4,5-diamine; 1-(2,4-dimethylphenyl)-3-methoxy-1H-pyrazole-4,5-diamine; 3-methoxy-1-(pyridin-4-yl)-1H-pyrazole-4,5-diamine; 1-benzyl-3-methoxy-1H-pyrazole-4,5-diamine; 1-(4-aminobenzyl)-3-methoxy-1H-pyrazole-4,5-diamine; 3-cyano-1-(2-hydroxyethyl)-1H-pyrazole-4,5-diamine; 1-butyl-3-cyano-1H-pyrazole-4,5-diamine; 3-cyano-1-phenyl-1H-pyrazol-4,5-diamine; 3-cyano-1-(pyridin-2-yl)-1H-pyrazol-4,5-diamine; 3-cyano-1-(2,4-dimethylphenyl)-1H-pyrazol-4,5-diamino; 3-cyano-1-p-tolyl-1H-pyrazol-4,5-diamine; 3-cyano-1-(4-methoxyphenyl)-1H-pyrazol-4,5-diamine; 1-(4-aminophenyl)-3-cyano-1H-pyrazol-4,5-diamine; 3-cyano-1-(4-(dimethylamino)phenyl)-1H-pyrazol-4,5-diamine; 3-cyano-$N^5,N^5$-dimethyl-1-phenyl-1H-pyrazol-4,5-diamine; 3-cyano-$N^5,N^5$-dimethyl-1-pentyl-1H-pyrazole-4,5-diamine; 3-cyano-1-pentyl-5-(pyrrolidin-1-yl)-1H-pyrazol-4-amine; 3-cyano-1-octyl-1H-pyrazole-4,5-diamine; 3-cyano-1-hexyl-1H-pyrazol-4,5-diamine; 1-butyl-3-cyano-1H-pyrazol-4,5-diamine; 7-amino-6-cyano-2,3-dihydro-1H-imidazo[1,2-b]pyrazole; 3-amino-2-cyano-4,5,6,7-tetrahydropyrazolo[1,5-a]pyrimidine; 3-cyano-1-(4-methoxybenzyl)-1H-pyrazol-4,5-diamine; 1-benzyl-3-cyano-1H-pyrazol-4,5-diamine; 3-cyano-1-cyclohexyl-1H-pyrazol-4,5-diamine; 3-cyano-1-isopropyl-1H-pyrazol-4,5-diamine; 1-(3-aminopropyl)-3-cyano-1H-pyrazol-4,5-diamine; 3-cyano-$N^5$,1-(diisopropyl)-1H-pyrazol-4,5-diamine; $N^5$,1-diisopropyl-3-methoxy-1H-pyrazole-4,5-diamine; 3-bromo-$N^5$,1-diisopropyl-1H-pyrazole-4,5-diamine; 1-cyclohexyl-3-fluoro-$N^5$-isopropyl-1H-pyrazole-4,5-diamine; 1-methyl-3-(trifluoromethoxy)-1H-pyrazole-4,5-diamine; 1-pentyl-3-phenoxy-1H-pyrazole-4,5-diamine; 1-(3-methoxypropyl)-3-phenoxy-1H-pyrazole-4,5-diamine; 3-fluoro-1-octyl-1H-pyrazole-4,5-diamine; 3-chloro-1-hexyl-1H-pyrazole-4,5-diamine; 3-bromo-1-pentyl-1H-pyrazole-4,5-diamine; 3-fluoro-1-(2-hydroxyethyl)-1H-pyrazol-4,5-diamine; 3-chloro-1-(2-hydroxyethyl)-1H-pyrazol-4,5-diamine; 3-chloro-1-propyl-5-(pyrrolidin-1-yl)-1H-pyrazol-4-amine; 3-chloro-1-(4-hydroxybutyl)-1H-pyrazol-4,5-diamine; 3-fluoro-1-(3-(methylamino)propyl)-1H-pyrazole-4,5-diamine; 1-(3-(dimethylamino)propyl)-3-fluoro-$N^5,N^5$-dimethyl-1H-pyrazole-4,5-diamine; 6-chloro-1-methyl-2,3-dihydro-1H-imidazo[1,2-b]pyrazol-7-amine; 2-chloro-5,6,7,8-tetrahydro-4H-pyrazolo[1,5-a][1,3]diazepin-3-amine; 2-methoxy-5,6,7,8-tetrahydro-4H-pyrazolo[1,5-a][1,3]diazepin-3-amine; 2-methoxy-4-methyl-5,6,7,8-tetrahydro-4H-pyrazolo[1,5-a][1,3]diazepin-3-amine; 3-chloro-1-(pyridin-2-yl)-1H-pyrazole-4,5-diamine; 1-(5-aminopyridin-2-yl)-3-fluoro-1H-pyrazole-4,5-diamine; 3-fluoro-1-(4-methoxybenzyl)-1H-pyrazole-4,5-diamine; 3-chloro-1-phenyl-1H-pyrazole-4,5-diamine; 3-bromo-1-p-tolyl-1H-pyrazole-4,5-diamine; 1-benzyl-3-bromo-1H-pyrazole-4,5-diamine; 1-pentyl-3-phenoxy-1H-pyrazole-4,5-diamine; 1-(3-methoxypropyl)-3-phenoxy-1H-pyrazole-4,5-diamine; 1-(3-hydroxypropyl)-3-phenoxy-1H-pyrazole-4,5-diamine; 1-(3-aminopropyl)-$N^5$-methyl-3-phenoxy-1H-pyrazole-4,5-diamine; 3-chloro-$N^5,N^5$-dimethyl-1-pentyl-1H-pyrazole-4,5-diamine; 1-(3,5-dimethoxyphenyl)-3-fluoro-1H-pyrazole-4,5-diamine; 3-fluoro-1-methyl-1H-pyrazole-4,5-diamine; 3-chloro-1-ethyl-1H-pyrazole-4,5-diamine; 1-hexyl-3-(methylsulfonyl)-1H-pyrazole-4,5-diamine; 3-(methylsulfinyl)-1-octyl-1H-pyrazole-4,5-diamine; 1-cyclohexyl-3-(methylsulfonyl)-1H-pyrazole-4,5-diamine; 3-(methylsulfonyl)-1-phenyl-1H-pyrazole-4,5-diamine; 3-(methylsulfonyl)-1-propyl-1H-pyrazole-4,5-diamine; 1-(3-methoxypropyl)-3-(methylsulfinyl)-1H-pyrazole-4,5-diamine; 1-(3-hydroxypropyl)-3-(methylsulfinyl)-1H-pyrazole-4,5-diamine; 3-(methylsulfonyl)-1-propyl-5-(pyrrolidin-1-yl)-1H-pyrazol-4-amine; 1-butyl-3-(methylsulfonyl)-5-(piperidin-1-yl)-1H-pyrazol-4-amine; 1-methyl-3-(methylsulfonyl)-5-morpholino-1H-pyrazol-4-amine; 5-(4-ethylpiperazin-1-yl)-1-methyl-3-(methylsulfonyl)-1H-pyrazol-4-amine; 1-(4-(dimethylamino)phenyl)-3-(methylsulfonyl)-1H-pyrazole-4,5-diamine; 1-(4-methoxybenzyl)-3-(methylsulfonyl)-1H-pyrazole-4,5-diamine; $N^5$,1-diisopropyl-3-(methylsulfonyl)-1H-pyrazole-4,5-diamine; $N^5,N^5$-dimethyl-3-(methylsulfonyl)-1-pentyl-1H-pyrazole-4,5-diamine; 3-(methylsulfonyl)-1-o-tolyl-1H-pyrazole-4,5-diamine; 3-(methylsulfonyl)-1-(pyridin-2-yl)-1H-pyrazole-4,5-diamine; 3-(methylsulfinyl)-1-(pyrimidin-2-yl)-1H-pyrazole-4,5-diamine; 3-(methylsulfinyl)-1-(thiazol-2-yl)-1H-pyrazole-4,5-diamine; 1-(1-methyl-1H-imidazol-2-yl)-3-(methylsulfinyl)-1H-pyrazole-4,5-diamine; 3-(methylsulfonyl)-1-(thiazol-2-yl)-1H-pyrazole-4,5-diamine; 2-(methylsulfonyl)-5,6,7,8-tetrahydro-4H-pyrazolo[1,5-a][1,3]diazepin-3-amine; 6-(methylsulfonyl)-2,3-dihydro-1H-imidazo[1,2-b]pyrazol-7-amine; 1-methyl-3-(methylsulfinyl)-1H-pyrazole-4,5-diamine; 1-methyl-3-(methylsulfonyl)-1H-pyrazole-4,5-diamine; 1-(3-(methylamino)propyl)-3-(methylsulfonyl)-1H-pyrazole-4,5-diamine; 1-(2-aminoethyl)-3-(methylsulfinyl)-1H-pyrazole-4,5-diamine; 1-hexyl-3-(trifluoromethoxy)-1H-pyrazole-4,5-diamine; 2-(4,5-diamino-3-ethynyl-pyrazol-1-yl)-ethanol; 5-ethynyl-2-methyl-2H-pyrazole-3,4-diamine; 5-ethynyl-2-(2-methoxy-ethyl)-2H-pyrazole-3,4-diamine; 5-ethynyl-2-hexyl-2H-pyrazole-3,4-diamine; 5-ethynyl-2-phenyl-2H-pyrazole-3,4-diamine; 2-(4,5-diamino-3-phenylethynyl-pyrazol-1-yl)-ethanol; 2-benzyl-5-prop-1-ynyl-2H-pyrazole-3,4-diamine; 5-ethynyl-2-pyridin-2-yl-2H-pyrazole-3,4-diamine; 5-ethynyl-2-(1H-imidazol-4-ylmethyl)-2H-pyrazole-3,4-diamine; and 5-(4,5-diamino-3-ethynyl-pyrazol-1-yl)-pentane-1,2-diol.

2. A keratin dyeing composition comprising:
a. a medium suitable for dyeing; and
at least one compound of claim 1 and derivatives thereof.

3. The composition of claim 2 comprising a coupler compound selected from the group consisting of phenols, resorcinols, naphthols, m-aminophenols, m-phenylenediamines, heterocyclic compounds, and mixtures thereof.

4. The composition of claim 2 comprising a coupler compound selected from the group consisting of 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; 2-methyl-benzene-1,3-diol; 1-acetoxy-2-methylnaphthalene; benzene-1,3-diamine; 2-(2,4-diamino-phenoxy)-ethanol; 4-{3-[(2,4-diaminophenyl)oxy]propoxy}benzene-1,3-diamine; 2-[2,4-d]amino-5-(2-hydroxy-ethoxy)-phenoxy]-ethanol; 3-(2,4-diamino-phenoxy)-propan-1-ol; 2,4-diamino-5-(2'-hydroxyethyloxy)toluene; 1-methyl-2,6-bis(2-hydroxyethylamino)benzene; 3-amino-phenol; 5-amino-2-methyl-phenol; 3-amino-2,6-dimethylphenol; 3-amino-2-methyl-phenol; 1-methyl-2-hydroxy-4-(2'-hydroxyethyl)aminobenzene; 1-hydroxy-3-amino-2,4-dichlorobenzene; 1,3-Bis-(2,4-diaminophenoxy)propane; 1-hydroxy-2-methyl-5-amino-6-chlorobenzene; 5-amino-4-chloro-2-methylphenol; 3,4-dihydro-2H-1,4-benzoxazin-6-ol; 1,3-benzodioxol-5-ol; 1,3-benzodioxol-5-amine; 1H-indol-4-ol; 1H-indole-5,6-diol; 1H-indol-7-ol; 1H-indol-5-ol; 1H-indol-6-ol; pyridine-2,6-diamine; 2-aminopyridin-3-ol; 4-hydroxy-N-methylindole; 2,6-dihydroxypyridine; 6-hydroxybenzomorpholine; 3,5-diamino-2,6-dimethoxypyridine; 3-amino-2-methylamino-6-methoxypyridine; and mixtures thereof.

5. The composition of claim 2 comprising a developer compound selected from the group consisting of 2-(methoxymethyl)benzene-1,4-diamine; benzene-1,4-diamine; N,N-bis(2-hydroxyethyl)-p-phenylenediamine; 4-aminophenol; 4-methylamino-phenol; 4-amino-3-methyl-phenol; 2-amino-phenol; 2-amino-5-methyl-phenol; 2-amino-5-ethyl-phenol; 2-amino-6-methyl-phenol; 1-methyl-1H-pyrazole-4,5-diamine; 2-(4,5-diamino-1H-pyrazol-1-yl)ethanol; 2,5-diaminophenylethyl alcohol; and mixtures thereof.

6. The composition of claim 2 comprising at least one component selected from the group consisting of oxidizing agents, thickeners, chelants, pH modifiers, buffering agents, a carbonate ion source, a radical scavenger, and mixtures thereof.

7. The composition of claim 2 comprising a carbonate ion source.

8. The composition of claim 2 comprising a radical scavenger.

9. The composition of claim 2 comprising a carbonate ion source and a radical scavenger.

10. The composition of claim 2 comprising ammonium carbonate and sodium glycinate.

11. A method of dyeing hair comprising the steps of
(a) applying the composition of claim 2; and
(b) rinsing hair.

12. A kit comprising
(a) the composition of claim 2; and
(b) an oxidizing agent.

* * * * *